(12) United States Patent
Shelton, IV et al.

(10) Patent No.: US 12,011,164 B2
(45) Date of Patent: Jun. 18, 2024

(54) CARTRIDGE-BASED FIRING LOCKOUT MECHANISM FOR SURGICAL STAPLER

(71) Applicant: Cilag GmbH International, Zug (CH)

(72) Inventors: Frederick E. Shelton, IV, Hillsboro, OH (US); Kevin M. Fiebig, Cincinnati, OH (US); Adam D. Hensel, Cincinnati, OH (US); Gregory J. Bakos, Mason, OH (US)

(73) Assignee: Cilag GmbH International, Zug (CH)

( * ) Notice: Subject to any disclaimer, the term of this patent is extended or adjusted under 35 U.S.C. 154(b) by 0 days.

(21) Appl. No.: 17/402,720

(22) Filed: Aug. 16, 2021

(65) Prior Publication Data
US 2023/0051222 A1 Feb. 16, 2023

(51) Int. Cl.
*A61B 17/072* (2006.01)
*A61B 17/00* (2006.01)

(52) U.S. Cl.
CPC .. *A61B 17/072* (2013.01); *A61B 2017/00367* (2013.01); *A61B 2017/07271* (2013.01); *A61B 2017/07278* (2013.01)

(58) Field of Classification Search
CPC ........ A61B 17/072; A61B 2017/00367; A61B 2017/07271; A61B 2017/07278
USPC ..................................................... 227/175.3
See application file for complete search history.

(56) References Cited

U.S. PATENT DOCUMENTS

| | | |
|---|---|---|
| 5,129,570 A | 7/1992 | Schulze et al. |
| 5,465,895 A * | 11/1995 | Knodel ............ A61B 17/07207 227/176.1 |
| 7,380,695 B2 * | 6/2008 | Doll ................. A61B 17/07207 227/176.1 |
| 7,404,508 B2 | 7/2008 | Smith et al. |
| 7,434,715 B2 | 10/2008 | Shelton, IV et al. |
| 7,721,930 B2 | 5/2010 | McKenna et al. |
| 7,810,692 B2 | 10/2010 | Hall et al. |

(Continued)

FOREIGN PATENT DOCUMENTS

| | | |
|---|---|---|
| EP | 3498191 A2 | 6/2019 |
| WO | WO 2015/153642 A1 | 10/2015 |

(Continued)

OTHER PUBLICATIONS

U.S. Appl. No. 17/402,679.

(Continued)

*Primary Examiner* — Dariush Seif
(74) *Attorney, Agent, or Firm* — Frost Brown Todd LLP

(57) ABSTRACT

A surgical stapling instrument includes a shaft assembly and an end effector. The end effector includes a first jaw having an anvil, a second jaw configured to removably receive a staple cartridge, and a driving assembly translatable distally through the second jaw for pivoting the second jaw toward the first jaw to clamp tissue between the first jaw and the second jaw. The instrument also includes a lockout mechanism configured to transition between a first state in which the lockout mechanism prevents distal translation of the driving assembly through the second jaw, and a second state in which the lockout mechanism permits distal translation of the driving assembly through the second jaw. The lockout mechanism is configured to transition from the first state to the second state when the staple cartridge is removably received by the second jaw.

14 Claims, 12 Drawing Sheets

(56) References Cited

U.S. PATENT DOCUMENTS

| | | | |
|---|---|---|---|
| 7,832,408 B2 | 11/2010 | Shelton, IV et al. | |
| 7,845,537 B2 | 12/2010 | Shelton, IV et al. | |
| 8,083,120 B2 | 12/2011 | Shelton, IV et al. | |
| 8,210,411 B2 | 7/2012 | Yates et al. | |
| 8,408,439 B2 | 4/2013 | Huang et al. | |
| 8,453,914 B2 | 6/2013 | Laurent et al. | |
| 8,708,213 B2 | 4/2014 | Shelton, IV et al. | |
| 9,060,770 B2 | 6/2015 | Shelton, IV et al. | |
| 9,186,142 B2 | 11/2015 | Fanelli et al. | |
| 9,517,065 B2 | 12/2016 | Simms et al. | |
| 9,622,746 B2 | 4/2017 | Simms et al. | |
| 9,717,497 B2 | 8/2017 | Zerkle et al. | |
| 9,795,379 B2 | 10/2017 | Leimbach et al. | |
| 9,808,248 B2 | 11/2017 | Hoffman | |
| 9,839,487 B2 | 12/2017 | Dachs, II | |
| 10,011,018 B2 | 7/2018 | McGrogan et al. | |
| 10,092,292 B2 | 10/2018 | Boudreaux et al. | |
| 10,245,036 B1* | 4/2019 | Schaller | A61B 17/07207 |
| 10,307,170 B2 | 6/2019 | Parfett et al. | |
| 10,485,621 B2 | 11/2019 | Morrissette et al. | |
| 10,537,400 B2 | 1/2020 | Dachs, II et al. | |
| 10,610,313 B2 | 4/2020 | Bailey et al. | |
| 10,667,809 B2 | 6/2020 | Bakos et al. | |
| 10,806,530 B2 | 10/2020 | Liao et al. | |
| 10,863,988 B2 | 12/2020 | Patel et al. | |
| 11,020,138 B2 | 6/2021 | Ragosta | |
| 11,026,755 B2 | 6/2021 | Weir et al. | |
| 11,076,926 B2 | 8/2021 | Ragosta et al. | |
| 11,147,552 B2 | 10/2021 | Burbank et al. | |
| 11,166,773 B2 | 11/2021 | Ragosta et al. | |
| 11,234,700 B2 | 2/2022 | Ragosta et al. | |
| 11,259,884 B2 | 3/2022 | Burbank | |
| 11,311,293 B2* | 4/2022 | Roberts | A61B 17/0686 |
| 2004/0232200 A1* | 11/2004 | Shelton, IV | A61B 17/07207 227/176.1 |
| 2006/0185682 A1 | 8/2006 | Marczyk | |
| 2007/0102475 A1* | 5/2007 | Ortiz | A61B 17/07207 227/19 |
| 2010/0065604 A1* | 3/2010 | Weng | A61B 17/07207 227/180.1 |
| 2010/0301095 A1* | 12/2010 | Shelton, IV | A61B 17/068 227/175.4 |
| 2012/0209314 A1 | 8/2012 | Weir et al. | |
| 2013/0327808 A1* | 12/2013 | Chen | A61B 17/07207 227/175.2 |
| 2014/0224686 A1* | 8/2014 | Aronhalt | A61B 17/0644 206/339 |
| 2014/0263550 A1* | 9/2014 | Aranyi | A61B 17/07207 227/175.3 |
| 2015/0265275 A1* | 9/2015 | Chen | A61B 17/07207 227/175.3 |
| 2015/0272576 A1* | 10/2015 | Cappola | A61B 17/072 227/175.2 |
| 2015/0297228 A1 | 10/2015 | Huitema et al. | |
| 2015/0316431 A1* | 11/2015 | Collins | G01L 5/0028 227/176.1 |
| 2015/0374363 A1* | 12/2015 | Laurent, IV | A61B 17/105 227/176.1 |
| 2016/0157863 A1* | 6/2016 | Williams | A61B 17/068 227/175.2 |
| 2016/0361126 A1 | 12/2016 | Schena et al. | |
| 2017/0020617 A1 | 1/2017 | Weir et al. | |
| 2017/0265865 A1 | 9/2017 | Burbank | |
| 2017/0265954 A1 | 9/2017 | Burbank et al. | |
| 2017/0290584 A1* | 10/2017 | Jasemian | A61B 17/072 |
| 2017/0296190 A1* | 10/2017 | Aronhalt | A61B 17/068 |
| 2017/0333037 A1 | 11/2017 | Wellman et al. | |
| 2018/0168651 A1* | 6/2018 | Shelton, IV | A61B 34/30 |
| 2018/0168756 A1 | 6/2018 | Liao et al. | |
| 2018/0271608 A1 | 9/2018 | Ragosta et al. | |
| 2018/0310935 A1 | 11/2018 | Wixey | |
| 2018/0325606 A1 | 11/2018 | Weir et al. | |
| 2018/0344419 A1 | 12/2018 | Dachs, II et al. | |
| 2019/0038371 A1 | 2/2019 | Wixey et al. | |
| 2019/0076142 A1 | 3/2019 | Wixey | |
| 2019/0076143 A1 | 3/2019 | Smith | |
| 2019/0099181 A1* | 4/2019 | Shelton, IV | A61B 90/03 |
| 2019/0167266 A1 | 6/2019 | Patel et al. | |
| 2019/0183503 A1* | 6/2019 | Shelton, IV | A61B 90/06 |
| 2019/0192158 A1* | 6/2019 | Scott | A61B 17/2833 |
| 2019/0200989 A1 | 7/2019 | Burbank et al. | |
| 2019/0239967 A1 | 8/2019 | Ragosta et al. | |
| 2019/0261984 A1* | 8/2019 | Nelson | A61B 17/07207 |
| 2019/0262088 A1 | 8/2019 | Burbank | |
| 2020/0138529 A1 | 5/2020 | Ragosta et al. | |
| 2020/0268381 A1* | 8/2020 | Roberts | A61B 17/0686 |
| 2020/0397430 A1 | 12/2020 | Patel et al. | |
| 2020/0405301 A1 | 12/2020 | Shelton, IV et al. | |
| 2021/0393340 A1 | 12/2021 | Beckman et al. | |
| 2021/0401433 A1 | 12/2021 | Freidel et al. | |
| 2022/0133318 A1* | 5/2022 | Hudson | A61B 17/07207 227/175.1 |
| 2022/0211370 A1* | 7/2022 | Roberts | A61B 17/0686 |

FOREIGN PATENT DOCUMENTS

| | | |
|---|---|---|
| WO | WO 2017/083125 A1 | 5/2017 |
| WO | WO 2017/083129 A1 | 5/2017 |
| WO | WO 2018/049198 A1 | 3/2018 |
| WO | WO 2018/049206 A1 | 3/2018 |
| WO | WO 2018/049211 A1 | 3/2018 |
| WO | WO 2018/049217 A1 | 3/2018 |
| WO | WO 2018/052806 A1 | 3/2018 |
| WO | WO 2018/052810 A1 | 3/2018 |
| WO | WO 2018/071497 A1 | 4/2018 |
| WO | WO 2018/071763 A1 | 4/2018 |
| WO | WO 2018/085529 A2 | 5/2018 |
| WO | WO 2018/175467 A1 | 9/2018 |
| WO | WO 2019/165403 A1 | 8/2019 |
| WO | WO 2020/131290 A1 | 6/2020 |

OTHER PUBLICATIONS

U.S. Appl. No. 17/402,674, entitled "Surgical Stapler End Effector Sled Having Cartridge Wall Support Feature," filed Nov. 4, 2020.
U.S. Appl. No. 17/402,674, entitled "Methods of Operating a Robotic Surgical Stapler," filed Aug. 16, 2021.
U.S. Appl. No. 17/402,675, entitled "Multi-Threshold Motor Control Algorithm for Powered Surgical Stapler," filed Aug. 16, 2021.
U.S. Appl. No. 17/402,677, entitled "Variable Response Motor Control Algorithm for Powered Surgical Stapler," filed Aug. 16, 2021.
U.S. Appl. No. 17/402,679, entitled "Powered Surgical Stapler Having Independently Operable Closure and Firing Systems," filed Aug. 16, 2021.
U.S. Appl. No. 17/402,695, entitled "Powered Surgical Stapler Having Independently Operable Closure and Firing Systems," filed Aug. 16, 2021.
U.S. Appl. No. 17/402,701, entitled "Multiple-Sensor Firing Lockout Mechanism for Powered Surgical Stapler," filed Aug. 16, 2021.
U.S. Appl. No. 17/402,703, entitled "Proximally Located Firing Lockout Mechanism for Surgical Stapler," filed Aug. 16, 2021.
U.S. Appl. No. 17/402,732, entitled "Multi-Position Restraining Member for Sled Movement," filed Aug. 16, 2021.
U.S. Appl. No. 17/402,738, entitled "Firing Member Tracking Feature for Surgical Stapler," filed Aug. 16, 2021.
U.S. Appl. No. 17/402,744, entitled "Adjustable Power Transmission Mechanism for Powered Surgical Stapler," filed Aug. 16, 2021.
U.S. Appl. No. 17/402,749, entitled "Firing Bailout System for Powered Surgical Stapler," filed Aug. 16, 2021.
U.S. Appl. No. 17/402,759, entitled "Deflectable Firing Member for Surgical Stapler," filed Aug. 16, 2021.
U.S. Pat. Pub. No. 2023/0045893.
U.S. Pat. Pub. No. 2023/0045998.
U.S. Pat. Pub. No. 2023/0048444.
U.S. Pat. Pub. No. 2023/0049736.
U.S. Pat. Pub. No. 2023/0050358.
U.S. Pat. Pub. No. 2023/0050707.
U.S. Pat. Pub. No. 2023/0051105.

(56) References Cited

OTHER PUBLICATIONS

U.S. Pat. Pub. No. 2023/0051271.
U.S. Pat. Pub. No. 2023/0051361.
U.S. Pat. Pub. No. 2023/0051756.
U.S. Pat. Pub. No. 2023/0051938.
U.S. Pat. Pub. No. 2023/0052307.
International Search Report and Written Opinion dated Jan. 23, 2023, for International Application No. PCT/IB2022/057609, 15 pages.
U.S. Appl. No. 17/402,674.
U.S. Appl. No. 17/402,675.
U.S. Appl. No. 17/402,677.
U.S. Appl. No. 17/402,695.
U.S. Appl. No. 17/402,701.
U.S. Appl. No. 17/402,703.
U.S. Appl. No. 17/402,732.
U.S. Appl. No. 17/402,738.
U.S. Appl. No. 17/402,744.
U.S. Appl. No. 17/402,749.
U.S. Appl. No. 17/402,759.
U.S. Pat. No. 11,779,332.
European Search Report and Written Opinion dated Feb. 14, 2024 for Application No. EP 23196507.0, 12 pgs.

\* cited by examiner

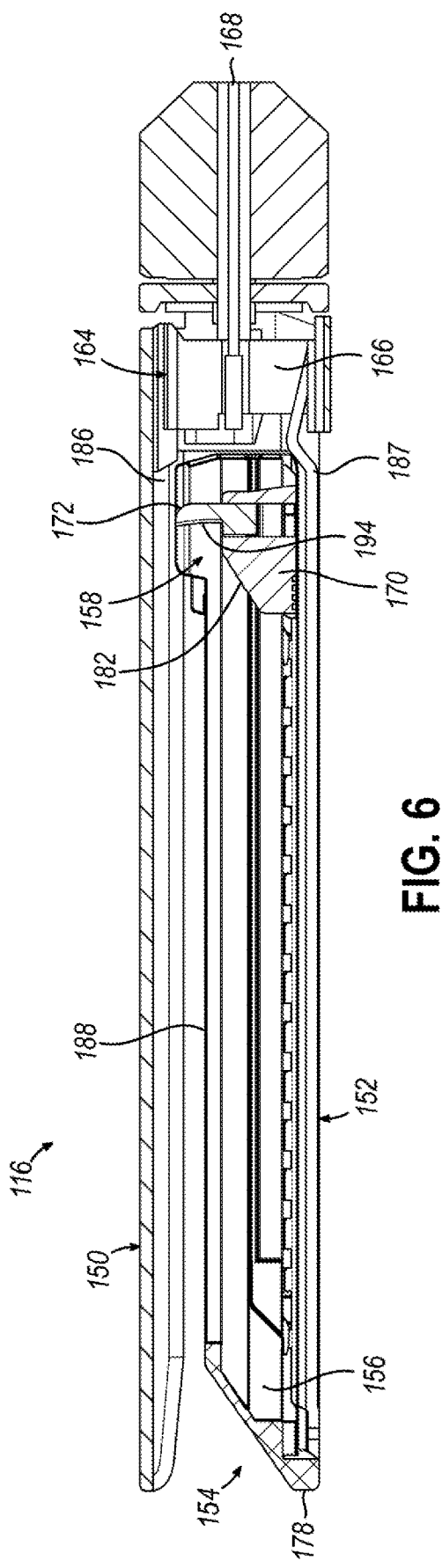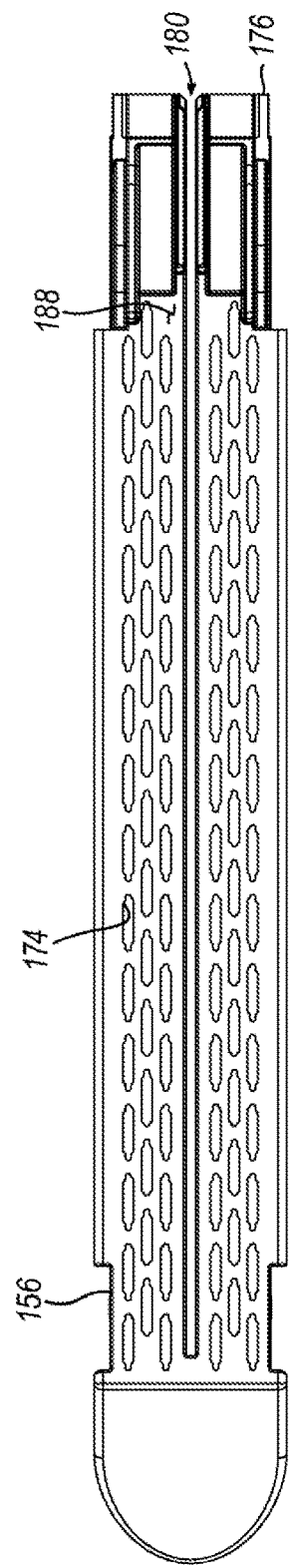
FIG. 6
FIG. 7

CARTRIDGE-BASED FIRING LOCKOUT MECHANISM FOR SURGICAL STAPLER

BACKGROUND

A variety of surgical instruments include an end effector for use in conventional medical treatments and procedures conducted by a medical professional operator, as well as applications in robotically assisted surgeries. Such surgical instruments may be directly gripped and manipulated by a surgeon or incorporated into robotically surgical systems. In the case of robotically assisted surgery, the surgeon may operate a master controller to remotely control the motion of such surgical instruments at a surgical site. The controller may be separated from the patient by a significant distance (e.g., across the operating room, in a different room, or in a completely different building than the patient). Alternatively, a controller may be positioned quite near the patient in the operating room. Regardless, the controller may include one or more hand input devices (such as joysticks, exoskeletal gloves, master manipulators, or the like), which are coupled by a servo mechanism to the surgical instrument. In one example, a servo motor moves a manipulator supporting the surgical instrument based on the surgeon's manipulation of the hand input devices. During the surgery, the surgeon may employ, via a robotic surgical system, a variety of surgical instruments including an ultrasonic blade, a surgical stapler, a tissue grasper, a needle driver, an electrosurgical cautery probe, etc. Each of these structures performs functions for the surgeon, for example, cutting tissue, coagulating tissue, holding or driving a needle, grasping a blood vessel, dissecting tissue, or cauterizing tissue.

Examples of surgical instruments include surgical staplers. Some such staplers are operable to clamp down on layers of tissue, cut through the clamped layers of tissue, and drive staples through the layers of tissue to substantially seal the severed layers of tissue together near the severed ends of the tissue layers. Examples of surgical staplers and associated features are disclosed in U.S. Pat. No. 7,404,508, entitled "Surgical Stapling and Cutting Device," issued Jul. 29, 2008; U.S. Pat. No. 7,434,715, entitled "Surgical Stapling Instrument Having Multistroke Firing with Opening Lockout," issued Oct. 14, 2008; U.S. Pat. No. 7,721,930, entitled "Disposable Cartridge with Adhesive for Use with a Stapling Device," issued May 25, 2010; U.S. Pat. No. 8,408,439, entitled "Surgical Stapling Instrument with An Articulatable End Effector," issued Apr. 2, 2013; U.S. Pat. No. 8,453,914, entitled "Motor-Driven Surgical Cutting Instrument with Electric Actuator Directional Control Assembly," issued Jun. 4, 2013; U.S. Pat. No. 9,186,142, entitled "Surgical Instrument End Effector Articulation Drive with Pinion and Opposing Racks," issued on Nov. 17, 2015; U.S. Pat. No. 9,795,379, entitled "Surgical Instrument with Multi-Diameter Shaft," issued Oct. 24, 2017; U.S. Pat. No. 9,808,248, entitled "Installation Features for Surgical Instrument End Effector Cartridge," issued Nov. 7, 2017; U.S. Pat. No. 10,092,292, entitled "Staple Forming Features for Surgical Stapling Instrument," issued Oct. 9, 2018; U.S. Pat. No. 9,717,497, entitled "Lockout Feature for Movable Cutting Member of Surgical Instrument," issued Aug. 1, 2017; U.S. Pat. No. 9,517,065, entitled "Integrated Tissue Positioning and Jaw Alignment Features for Surgical Stapler," issued Dec. 13, 2016; U.S. Pat. No. 9,622,746, entitled "Distal Tip Features for End Effector of Surgical Instrument," issued Apr. 18, 2017; and U.S. Pat. No. 8,210,411, entitled "Motor-Driven Surgical Instrument," issued Jul. 3, 2012. The disclosure of each of the above-cited U.S. Patents is incorporated by reference herein in its entirety.

While several surgical instruments and systems have been made and used, it is believed that no one prior to the inventors has made or used the invention described in the appended claims.

BRIEF DESCRIPTION OF THE DRAWINGS

While the specification concludes with claims which particularly point out and distinctly claim this technology, it is believed this technology will be better understood from the following description of certain examples taken in conjunction with the accompanying drawings, in which like reference numerals identify the same elements and in which:

FIG. 6 depicts a side cross-sectional view of the end effector of FIG. 4, where the end effector includes a staple cartridge;

FIG. 7 depicts a top view of a deck of the staple cartridge of FIG. 6;

Figure 1:
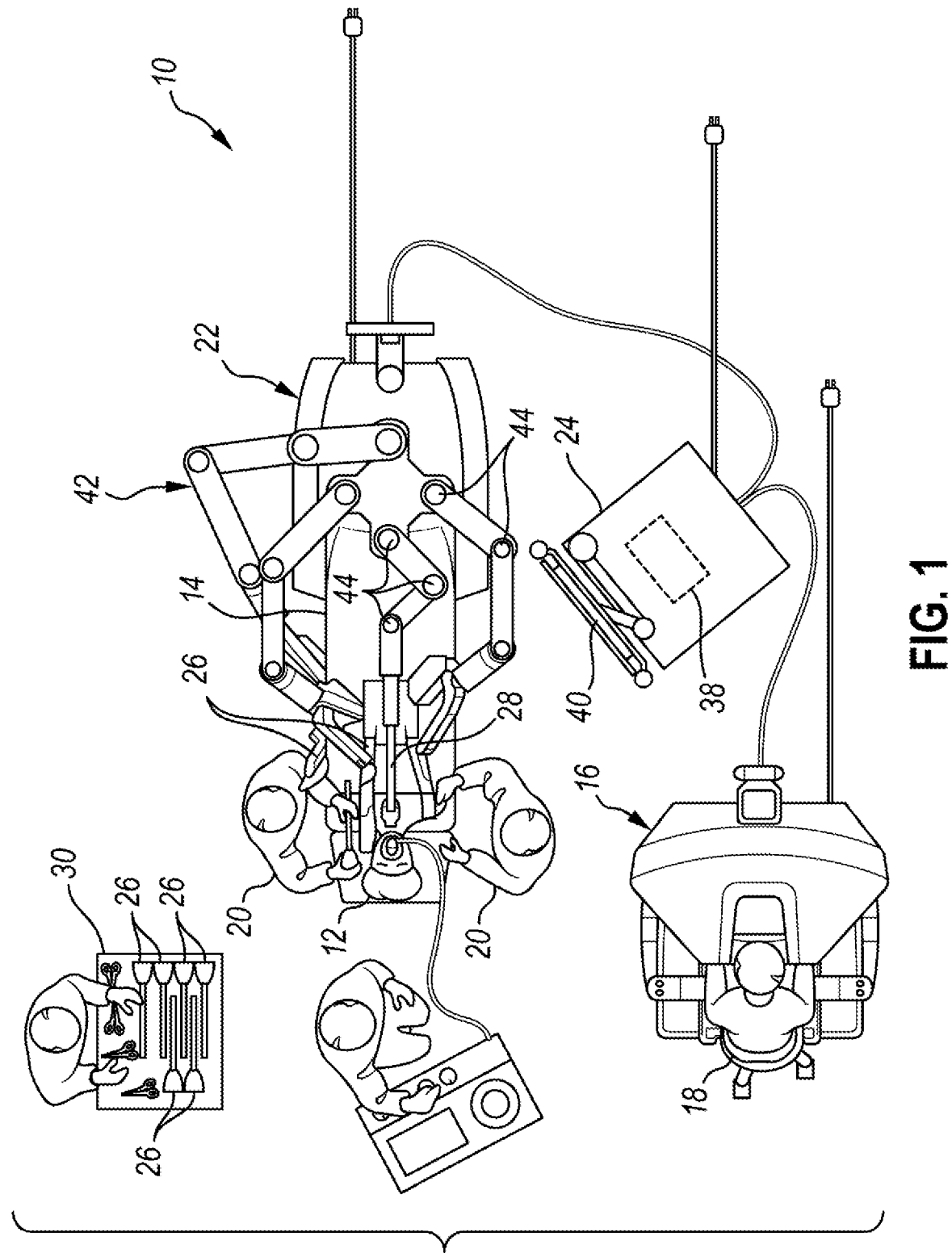
FIG. 1 depicts a top plan view of a robotic surgical system being used to perform a surgical procedure.

The drawings are not intended to be limiting in any way, and it is contemplated that various embodiments of the technology may be carried out in a variety of other ways, including those not necessarily depicted in the drawings. The accompanying drawings incorporated in and forming a part of the specification illustrate several aspects of the present technology, and together with the description serve to explain the principles of the technology; it being understood, however, that this technology is not limited to the precise arrangements shown.

DETAILED DESCRIPTION

The following description of certain examples of the technology should not be used to limit its scope. Other examples, features, aspects, embodiments, and advantages of the technology will become apparent to those skilled in the art from the following description, which is by way of illustration, one of the best modes contemplated for carrying out the technology. As will be realized, the technology described herein is capable of other different and obvious aspects, all without departing from the technology. Accordingly, the drawings and descriptions should be regarded as illustrative in nature and not restrictive.

It is further understood that any one or more of the teachings, expressions, embodiments, examples, etc. described herein may be combined with any one or more of the other teachings, expressions, embodiments, examples, etc. that are described herein. The following-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

For clarity of disclosure, the terms "proximal" and "distal" are defined herein relative to a human or robotic operator of the surgical instrument. The term "proximal" refers the position of an element closer to the human or robotic operator of the surgical instrument and further away from the surgical end effector of the surgical instrument. The term "distal" refers to the position of an element closer to the surgical end effector of the surgical instrument and further away from the human or robotic operator of the surgical instrument. It will be further appreciated that, for convenience and clarity, spatial terms such as "clockwise," "counterclockwise," "inner," "outer," "upper," "lower," and the like also are used herein for reference to relative positions and directions. Such terms are used below with reference to views as illustrated for clarity and are not intended to limit the invention described herein.

Aspects of the present examples described herein may be integrated into a robotically-enabled medical system, including as a robotic surgical system, capable of performing a variety of medical procedures, including both minimally invasive, such as laparoscopy, and non-invasive, such as endoscopy, procedures. Among endoscopy procedures, the robotically-enabled medical system may be capable of performing bronchoscopy, ureteroscopy, gastroscopy, etc.

I. Exemplary Robotic Surgical System

A. Overview

FIG. 1 shows a top plan view of an exemplary robotic surgical system (10) that may be used for performing a diagnostic or surgical procedure on a patient (12) who is lying down on an operating table (14). Robotic surgical system (10) may be constructed and operable in accordance with at least some of the teachings of U.S. Pat. No. 9,839,487, entitled "Backup Latch Release for Surgical Instrument," issued Dec. 12, 2017; U.S. Pat. No. 10,485,621, entitled "Sterile Barrier Between Surgical Instrument and Teleoperated Actuator," issued Nov. 26, 2019; U.S. Pat. No. 10,806,530, entitled "System and Method for Patient-Side Instrument Control," issued Oct. 20, 2020; U.S. Pat. No. 10,537,400, entitled "Detection Pins to Determine Presence of Surgical Instrument and Adapter on Manipulator," issued Jan. 21, 2020; U.S. Pat. No. 10,863,988, entitled "Surgical Instrument with Lockout Mechanism," published Dec. 15, 2020; U.S. Pat. No. 10,610,313, entitled "Surgical Instrument with Shiftable Transmission," issued Apr. 7, 2020; U.S. Pub. No. 2018/0271608, entitled "Manual Release for Medical Device Drive System," published Sep. 27, 2018, issued as U.S. Pat. No. 11,076,926 on Aug. 3, 2021; U.S. Pub. No. 2018/0325606, entitled "Systems and Methods for Operating an End Effector," published Nov. 15, 2018, issued as U.S. Pat. No. 11,026,755 on Jun. 8, 2021; U.S. Pub. No. 2019/0200989, entitled "Stapler Reload Detection and Identification," published Jul. 4, 2019, issued as U.S. Pat. No. 11,364,029 on Jun. 21, 2022; U.S. Pub. No. 2019/0239967, entitled "Stapler Beam Architecture," published Aug. 8, 2019, issued as U.S. Pat. No. 11,166,773 on Nov. 9, 2021; U.S. Pub. No. 2019/0262088, entitled "Robotic Surgical Stapler Assembly Configured to Use Stapler Reload," published Aug. 29, 2019, issued as U.S. Pat. No. 11,259,884 on Mar. 1, 2022; U.S. Pub. No. 2019/0239877, entitled "Wrist Architecture," published Aug. 8, 2019, issued as U.S. Pat. No. 11,234,700 on Feb. 1, 2022; U.S. Pub. No. 2019/

0201150, entitled "Push-Pull Surgical Instrument End Effector Actuation Using Flexible Tension Member," published Jul. 4, 2019, issued as U.S. Pat. No. 11,020,138 on Jun. 1, 2021; U.S. Pub. No. 2019/0282233, entitled "Stapler Cartridge With an Integral Knife," published Sep. 19, 2019, issued as U.S. Pat. No. 11,147,552 on Oct. 19, 2021; U.S. Pub. No. 2019/0262088, entitled "Robotic Surgical Stapler Assembly Configured to Use Stapler Reload," published Aug. 29, 2019, issued as U.S. Pat. No. 11,259,884 on Mar. 1, 2022; U.S. Pub. No. 2020/0138529, entitled "Locking System for Medical Device Drive System," published May 7, 2020, issued as U.S. Pat. No. 11,633,239 on Apr. 25, 2023; and/or U.S. Pub. No. 2020/0397430, entitled "Surgical Instrument With Lockout Mechanism," published Dec. 24, 2020, issued as U.S. Pat. No. 11,439,390 on Sep. 13, 2022. The disclosure of each of the above-cited U.S. Patents and U.S. Patent Publications is incorporated by reference herein in its entirety.

Robotic surgical system (10) may include a surgeon's console (16) for use by a surgeon (18) during a surgical procedure. One or more assistants (20) may also participate in the procedure. Robotic surgical system (10) may include a patient side cart (22) (i.e., a surgical robot) and an electronics cart (24). Patient side cart (22) may manipulate at least one surgical instrument (26) (also referred to as a "tool assembly" or "tool") through an incision in the body of patient (12) while surgeon (18) views the surgical site through surgeon's console (16). As will be described in greater detail below, surgical instrument(s) (26) and an imaging device (shown as an endoscope (28)) may be removably coupled with patient side cart (22). Electronics cart (24) may be used to process the images of the surgical site for subsequent display to the surgeon (18) through surgeon's console (16). Electronics cart (24) may be coupled with endoscope (28) and may include a processor (38) (shown schematically) to process captured images for subsequent display, such as to surgeon (18) on the surgeon's console (16), on a display (40) of electronics cart (24), or another suitable display located locally and/or remotely. The images may also be processed by a combination of electronics cart (24) and processor (38), which may be coupled together to process the captured images jointly, sequentially, and/or combinations thereof. Electronics cart (24) may overlay the captured images with a virtual control interface prior to displaying combined images to the surgeon (18) via surgeon's console (16).

Figure 2:
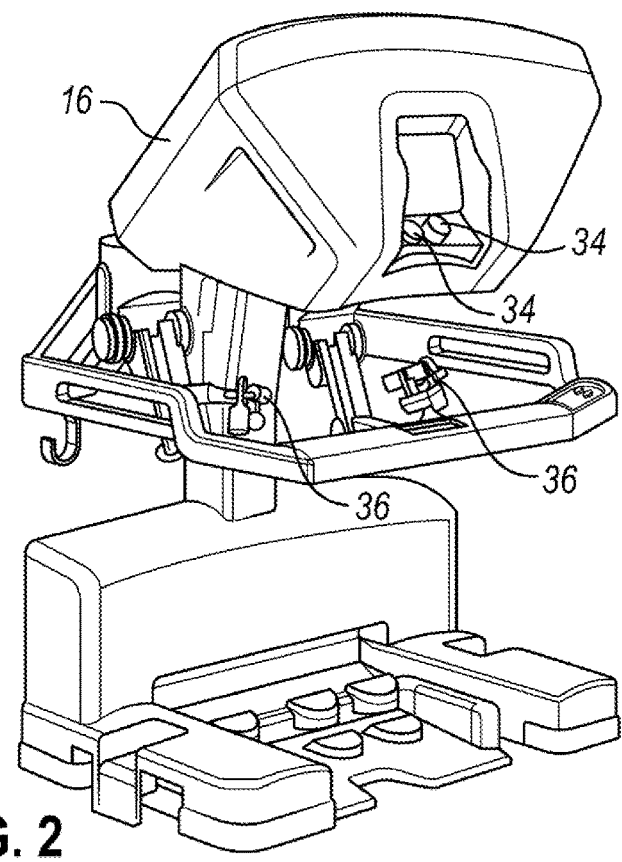
FIG. 2 depicts a perspective view of a surgeon's control console of the robotic surgical system of FIG. 1.

FIG. 2 shows a perspective view of surgeon's console (16). Surgeon's console (16) includes a left eye display (32) and a right eye display (34) for presenting surgeon (18) with a coordinated stereo view of the surgical site that enables depth perception. Surgeon's console (16) includes one or more input control devices (36) causing patient side cart (22) (shown in FIG. 1) to manipulate one or more surgical instruments (26). Input control devices (36) may provide the same degrees of freedom as their associated surgical instruments (26) (shown in FIG. 1) to provide surgeon (18) with telepresence, or the perception that the input control devices (36) are integral with surgical instruments (26). To this end, position, force, and tactile feedback sensors (not shown) may be employed to transmit position, force, and tactile sensations from surgical instruments (26) back to the surgeon's hands through input control devices (36). In some instances, surgeon's console (16) may be located in the same room as the patient so that surgeon (18) may directly monitor the procedure, be physically present if necessary, and speak to an assistant directly rather than over the telephone or other communication medium. Alternatively, surgeon (18) may be located in a different room, a completely different building, or other remote location from the patient allowing for remote surgical procedures.

Figure 3:
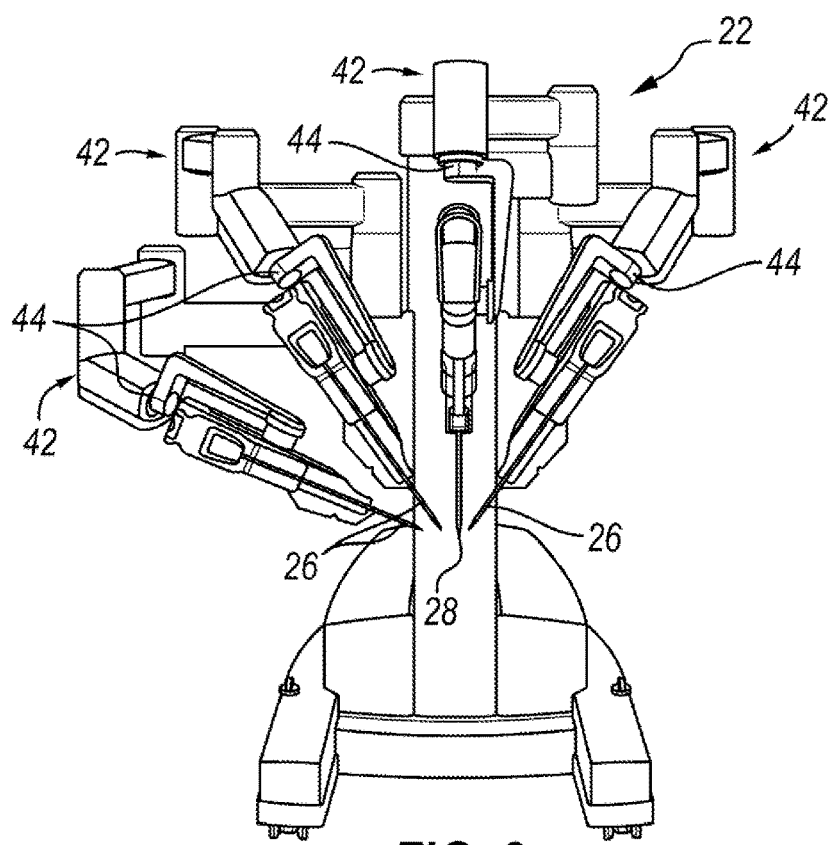
FIG. 3 depicts a front elevation view of a patient side cart of the robotic surgical system of FIG. 1.

FIG. 3 shows patient side cart (22) that manipulates surgical instruments (26). An image of the surgical site may be obtained by endoscope (28), which may include a stereoscopic endoscope. Manipulation is provided by robotic mechanisms, shown as robotic arms (42) that include at least one robotic joint (44) and an output coupler (not shown) that is configured to removable secure surgical instrument (26) with robotic arm (42). Endoscope (28) and surgical tools (26) may be positioned and manipulated through incisions in the patient so that a kinematic remote center is maintained at the incision to minimize the size of the incision. Images of the surgical site may include images of the distal ends of the surgical instruments (26) when they are positioned within the field-of-view of the endoscope (28). Patient side cart (22) may output the captured images for processing outside electronics cart (24). The number of surgical instruments (26) used at one time will generally depend on the diagnostic or surgical procedure and the space constraints within the operating room, among other factors. To change one or more of surgical instruments (26) being used during a procedure, assistant(s) (20) may remove surgical instrument (26) from patient side cart (22) and replace surgical instrument (26) with another surgical instrument (26) from a tray (30) (shown in FIG. 1) in the operating room.

B. Exemplary Surgical Instrument

Figure 4:
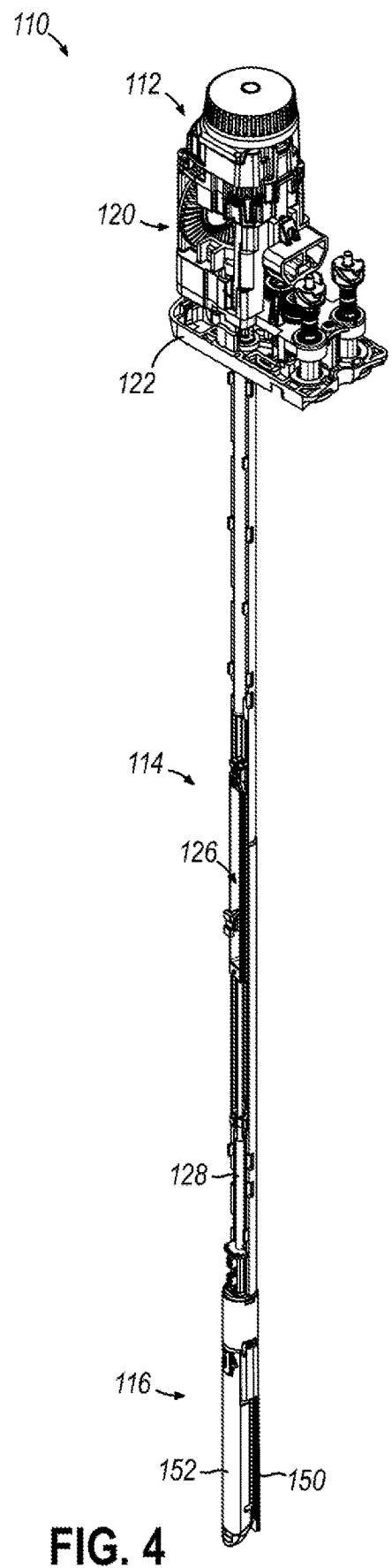
FIG. 4 depicts a perspective view of an exemplary surgical instrument that may be used with the robotic surgical system of FIG. 1, where the surgical instrument includes an instrument base, an elongate shaft, and an end effector, with select portions of the surgical instrument omitted to reveal internal features.
Figure 5:
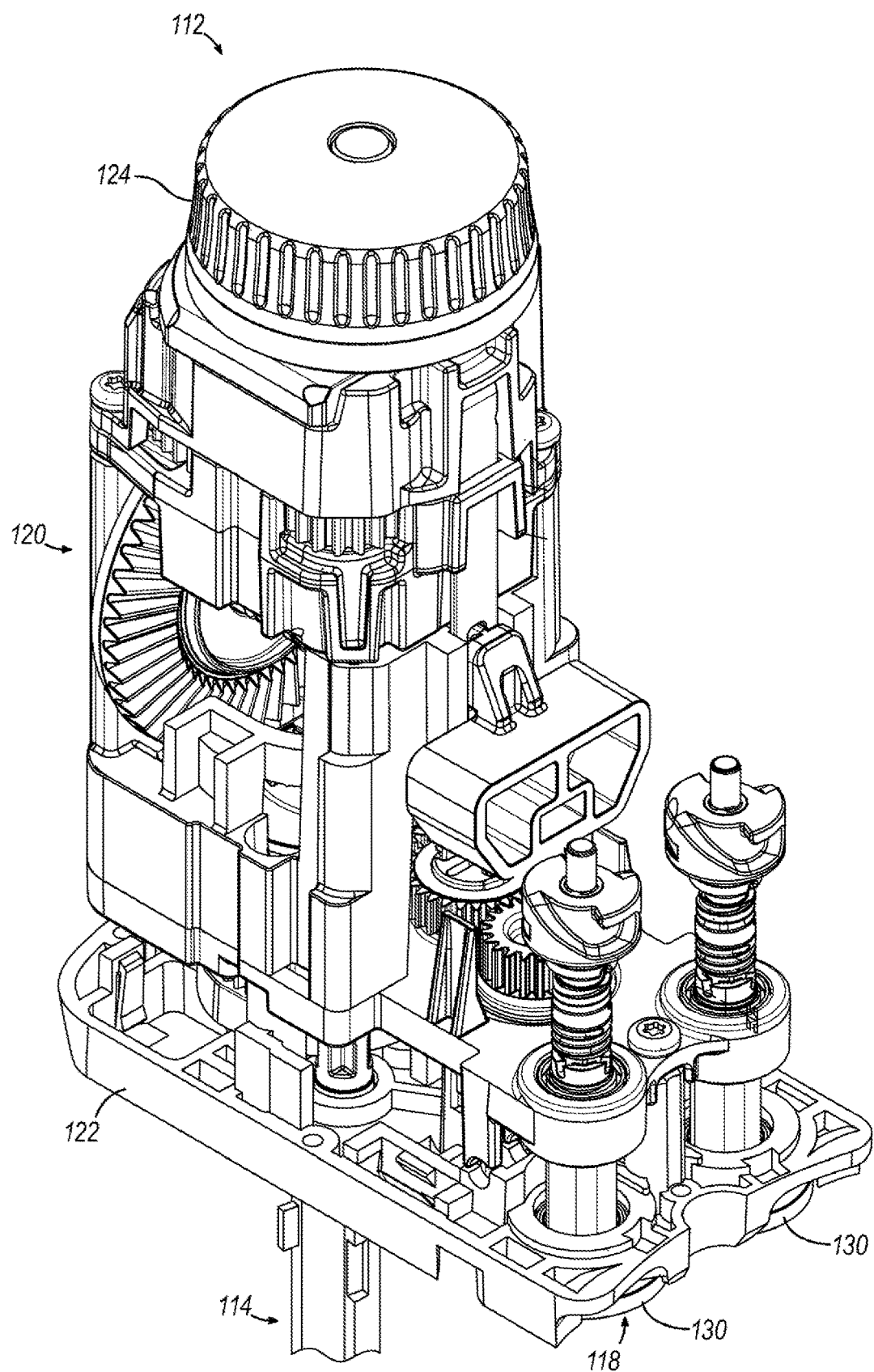
FIG. 5 depicts an enlarged perspective view of the instrument base of the surgical instrument of FIG. 4, with an outer housing omitted to reveal internal features.

FIGS. 4-5 show an exemplary surgical instrument (110) that may be mounted on and used with patient side cart (22) shown in FIG. 3. Surgical instrument (110) can have any of a variety of configurations capable of performing one or more surgical functions. As shown, surgical instrument (110) includes an instrument base (112), a shaft assembly (114) extending distally from instrument base (112), and an end effector (116) at a distal end of shaft assembly (114). Instrument base (112) includes an attachment interface (118) that includes input couplers (130) that are configured to interface with and be driven by corresponding output couplers (not shown) of robotic arm (42) of patient side cart (22).

FIG. 5 shows an enlarged perspective view of instrument base (112) of surgical instrument (110). Instrument base (112) includes a drive system (120) mounted on a chassis (122) and having one or more actuators for actuating end effector (116) to clamp, staple, and cut tissue, and for articulating end effector (116) relative to a longitudinal axis defined by shaft assembly (114). Drive system (120) may include a manual actuator (124), which is shown in the form of a knob configured to be manually rotated. Manual actuator (124) may engage other components of surgical instrument (110) to serve as a "bailout" mechanism to obtain a desired movement in end effector (116) without powered actuation of drive system (120). Shaft assembly (114) may include additional drive components, such as portions of a drive train (126), that may couple instrument base (112) to a moveable feature (128) of shaft assembly (114) that may be coupled to end effector (116). Shaft assembly (114) may be configured for use with a variety of interchangeable end effectors (116), such as a cutter, grasper, a cautery tool, a camera, a light, or a surgical stapler, for example.

C. First Exemplary End Effector

FIG. 6 shows a cross-sectional side view of end effector (116) of surgical instrument (110). End effector (116)

extends distally from a distal end of shaft assembly (114). In the present example, end effector (116) comprises a surgical stapler, which may also be referred to herein as an "endocutter," configured to clamp, cut, and staple tissue. As illustrated, end effector (116) includes opposing upper and lower jaws (150, 152) configured to move relative to one another between open and closed positions for clamping and releasing tissue.

One or both of upper and lower jaws (150, 152) may be configured to pivot and thereby actuate end effector (116) between open and closed positions. Lower jaw (152) includes a removable staple cartridge (154). In the illustrated example, lower jaw (152) is pivotable relative to upper jaw (150) to move between an open, unclamped position and a closed, clamped position. In other examples, upper jaw (150) may move relative to lower jaw (152) (e.g., similar to end effector (210) of FIGS. 9-10). In still other examples, both and upper and lower jaws (150, 152) may move to actuate end effector (116) between open and closed positions. In the present example, lower jaw (152) is referred to as a "cartridge jaw" or "channel jaw," and upper jaw (150) is referred to as an "anvil jaw."

Figure 8:
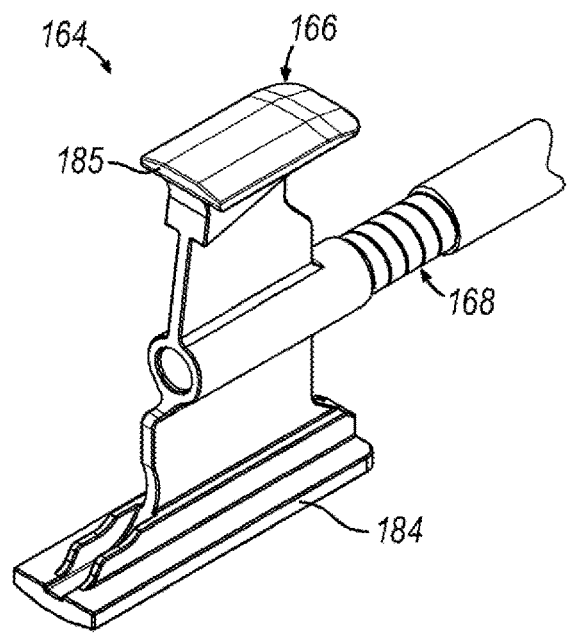
FIG. 8 depicts a driving assembly configured for use with the staple cartridge of FIG. 7.
Figure 9:
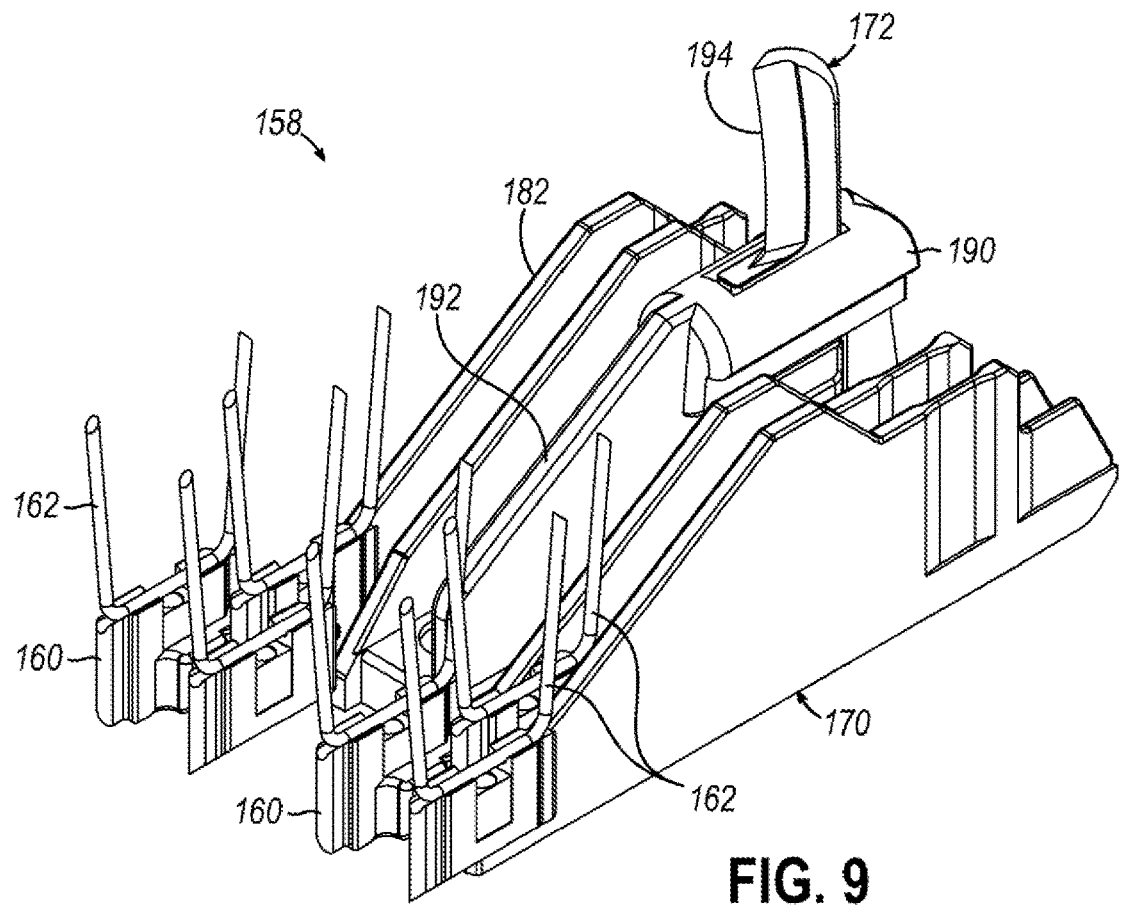
FIG. 9 depicts a firing assembly, staple drivers, and staples configured for use with the staple cartridge of FIG. 7.

Upper jaw (150) defines a surface that has a plurality of pockets (not shown) and operates as an anvil to deform staples ejected from staple cartridge (154) during operation. Staple cartridge (154) is replaceable, for example, by removing a used staple cartridge (154) from end effector (116) and inserting a new staple cartridge (154) into lower jaw (152). Staple cartridge (154) includes a staple cartridge body (156) that houses a firing assembly (158), a plurality of staple drivers (160) (also referred to as staple pushers), and a plurality of staples (162). As shown in FIGS. 6 and 8, end effector (116) includes a driving assembly (164) that includes a pusher member (166) that is operatively coupled with an actuation mechanism via a push rod (168). As shown in FIG. 6 and FIG. 9, firing assembly (158) includes a wedge sled (170) (also referred to as a staple pushing shuttle), and a knife member (172).

FIG. 7 shows a top view of staple cartridge body (156). Staple cartridge body (156) includes an array of staple accommodating apertures (174) (also known as openings) extending through an upper deck (188) of staple cartridge body (156). Each aperture (174) slidably houses a respective staple (162) in an unformed state and a free end of a corresponding staple driver (160) positioned beneath the unformed staple (162). Staple cartridge (154) includes proximal and distal ends (176, 178). In operation, staples (162) are sequentially deployed from apertures (174) by staple drivers (160) starting at proximal end (176) and advancing toward distal end (178). A vertical slot (180), configured to accommodate knife member (172), extends through part of staple cartridge (154).

FIG. 8 shows pusher member (166) as including first and second flanges (184, 185). First flange (184) is configured to be received in a longitudinal slot (186) (shown in FIG. 6) of upper jaw (150) and second flange (185) is configured to be received in a longitudinal slot (187) (shown in FIG. 6) of staple cartridge body (156) of lower jaw (152). First and second flanges (184, 185) move along longitudinal slots (186, 187) during actuation of pusher member (166). In some versions, pusher member (166) may include a single flange (e.g., omitting first flange (184)). As shown, longitudinal slot (186) is generally enclosed and longitudinal slot (187) opens to an exterior surface of lower jaw (152).

FIG. 9 shows a perspective view of firing assembly (158), which is configured to be slidably received within the proximal end of staple cartridge body (156) in a longitudinal direction prior to engaging staple drivers (160) and staples (162). Wedge sled (170) of firing assembly (158) slidingly interfaces with staple cartridge body (156). More specifically, wedge sled (170) advances distally along staple cartridge body (156) such that ramp portions (182) of wedge sled contact staple drivers (160). Staple drivers (160) push staples (162) out of apertures (174) of staple cartridge body (156) to penetrate through and staple tissue clamped between staple cartridge body (156) and upper jaw (150). An initial distal actuation of pusher member (166) may move pusher member (166) into contact with wedge sled (170), with further actuation pushing staples (162) transversely out of staple cartridge body (156).

At an initial proximal position of wedge sled (170), knife member (172) is housed within staple cartridge body (156). The position of knife member (172) is controlled during a first portion of the movement of wedge sled (170) from proximal end (176) of staple cartridge body (156) to distal end (178) of staple cartridge (154), so that a cutting edge (194) of knife member (172) extends through vertical slot (180). Vertical slot (180) accommodates cutting edge (194) of knife member (172) as firing assembly (158) is moved toward distal end (178) of staple cartridge (154). Wedge sled (170) includes a guide member (190) that provides a bearing surface that cooperates with a similarly shaped surface of staple cartridge body (156) to guide wedge sled (170). Guide member (190) extends from a vertical rib member (192) of wedge sled (170), which forms a central portion of wedge sled (170). In some versions, knife member (172), or at least cutting edge (194), may be retracted below upper deck (188) of staple cartridge body (156) prior to firing assembly (158) reaching its distal most position adjacent to distal end (178) of staple cartridge (154).

D. Second Exemplary End Effector

Figure 10:
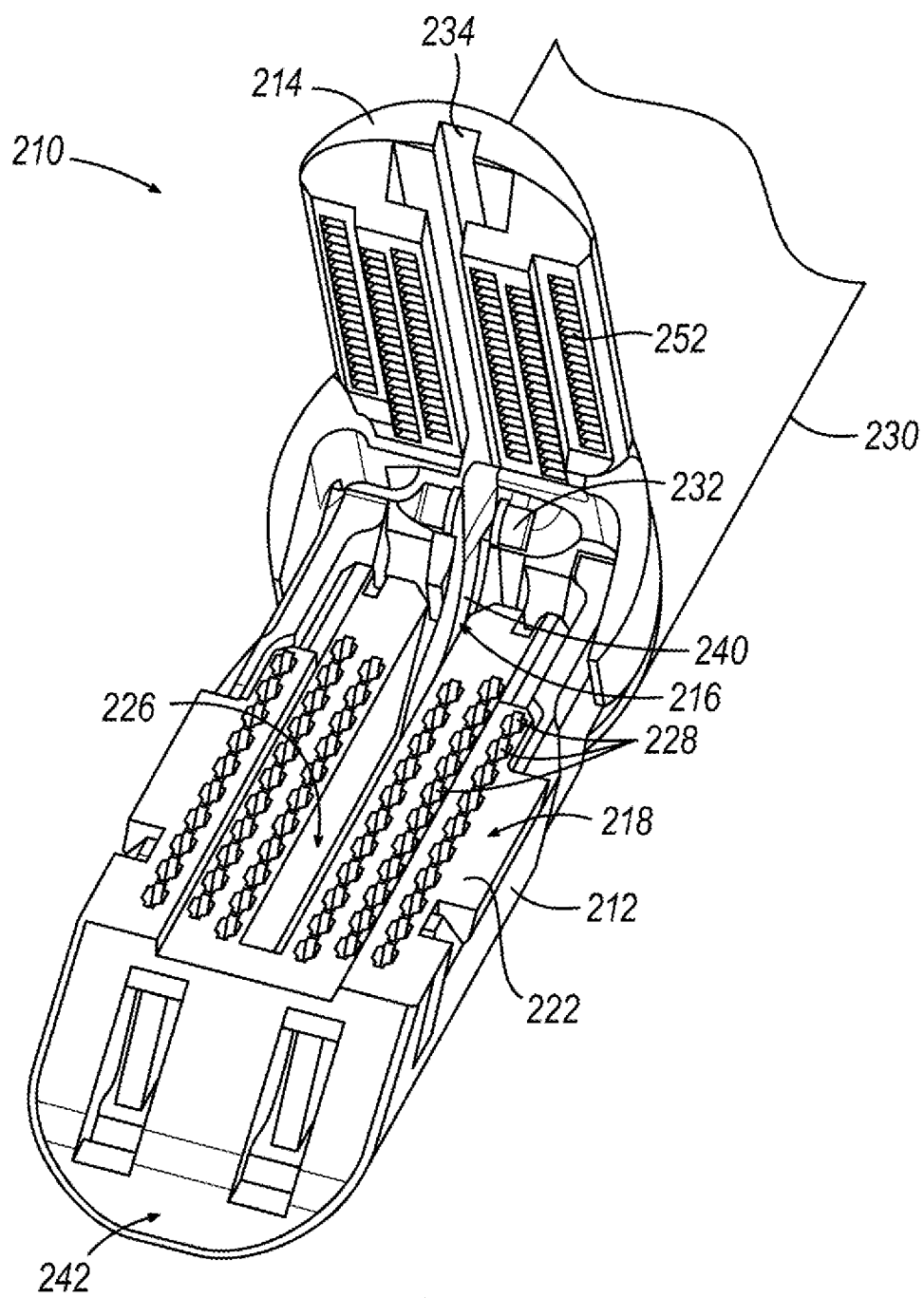
FIG. 10 depicts a second exemplary end effector that may be configured for use with the robotic surgical system of FIG. 1.
Figure 11:
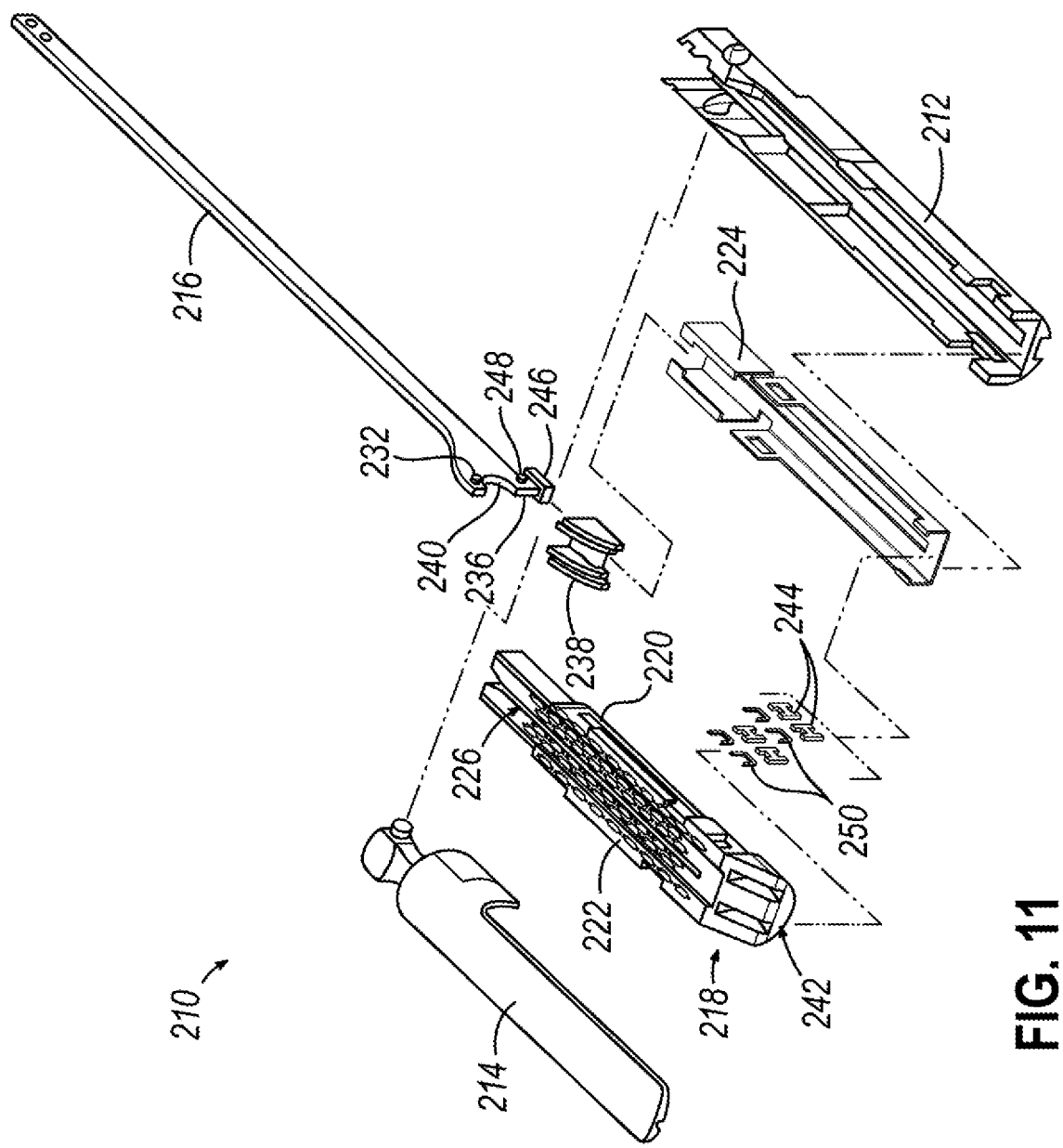
FIG. 11 depicts an exploded view of the end effector of FIG. 10.

FIGS. 10-11 show a second exemplary end effector (210), in an open position, that is configured to compress, cut, and staple tissue. End effector (210) may be configured for use with surgical instrument (110) of FIG. 4, or with surgical instruments of alternative constructions. End effector (210) may be constructed and operable in accordance with at least some of the teachings of U.S. patent application Ser. No. 16/916,295, entitled "Surgical Stapler Cartridge Retainer with Ejector Feature," filed Aug. 3, 2020, issued as U.S. Pat. No. 11,497,494 on Nov. 15, 2022, the disclosure of which is incorporated by reference herein in its entirety. End effector (210) of the present example includes a lower jaw (212) and an upper jaw in the form of a pivotable anvil (214). Lower jaw (212) may be constructed and operable in accordance with at least some of the teachings of U.S. Pat. No. 9,808,248, entitled "Installation Features for Surgical Instrument End Effector Cartridge," issued Nov. 7, 2017, the disclosure of which is incorporated by reference herein in its entirety. Anvil (214) may be constructed and operable in accordance with at least some of the teachings of U.S. Pat. No. 10,092,292, entitled "Staple Forming Features for Surgical Stapling Instrument," issued Oct. 9, 2018, the disclosure of which is incorporated by reference herein in its entirety.

FIG. 10 shows end effector (210), where anvil (214) is pivoted to an open position and a firing beam (216) is proximally positioned, allowing an unspent staple cartridge (218) to be removably installed into a channel of lower jaw (212). Staple cartridge (218) includes a cartridge body (220), which presents an upper deck (222) and is coupled with a lower cartridge tray (224). A vertical slot (226) is formed through part of staple cartridge (218) and opens upwardly through upper deck (222). One or more rows of staple apertures (228) are formed through upper deck (222) on one side of vertical slot (226), with one or more rows of staple apertures (228) being formed through upper deck (222) on the other side of vertical slot (226). End effector (210) is closed by distally advancing a closure tube (not shown) and a closure ring (230). Firing beam (216) is then advanced distally so that an upper pin of firing beam (216) enters longitudinal anvil slot (234). Simultaneously, a pusher block (236) located at the distal end of firing beam (216) engages a wedge sled (238) housed within cartridge body (220), such that wedge sled (238) is pushed distally by pusher block (236) as firing beam (216) is advanced distally through staple cartridge (218) and anvil (214).

During firing, cutting edge (240) of firing beam (216) enters vertical slot (226) toward distal end (242) of staple cartridge (218), severing tissue clamped between staple cartridge (218) and anvil (214). As best seen in FIG. 11, wedge sled (238) presents inclined cam surfaces that urge staple drivers (244) upwardly as wedge sled (238) is driven distally through staple cartridge (218). A firing beam cap (246) slidably engages a lower surface of lower jaw (212). Wedge sled (238) is movable longitudinally within staple cartridge (218), while staple drivers (244) are movable vertically within staple cartridge (218). A middle pin (248) and pusher block (236) of firing beam (216) together actuate staple cartridge (218) by entering into vertical slot (226) within staple cartridge (218), driving wedge sled (238) distally into upward camming contact with staple drivers (244) that in turn drive staples (250) out through staple apertures (228) and into forming contact with staple forming pockets (252) on the inner surface of anvil (214). Additional examples of alternative surgical instruments and/or associated features are described in U.S. patent application Ser. No. 16/946,363, entitled "Articulation Mechanisms for Robotic Surgical Tools," filed on Jun. 18, 2020, published as U.S. Pub. No. 2021/0393340 on Dec. 23, 2021, the disclosure of which is hereby incorporated by reference herein in its entirety.

It will be appreciated that any one or more of the teachings described below may be combined with any one or more of the teachings described above in connection with FIGS. 1-11.

II. Exemplary Cartridge-Based Firing Lockout Mechanisms for Surgical Stapler

In some instances, it may be desirable to provide surgical instrument (110) with a lockout feature for preventing a firing member of end effector (116), such as push rod (168), from actuating pusher member (166) distally when staple cartridge (154) is either spent, or otherwise improperly installed within or entirely absent from the channel of lower jaw (152) of end effector (116). Such prevention of distal actuation of pusher member (166) in the absence of a full staple cartridge (154) (also referred to as an "unspent" staple cartridge) that is properly seated may prevent inadvertent and improper closing of end effector (116) on tissue and resulting misalignment between staple cartridge (154) and anvil (214) that yields improper staple formation, which could otherwise occur via distal advancement of second flange (185) of pusher member (166) along longitudinal slot (187) of lower jaw (152). Such prevention of distal actuation of pusher member (166) in the absence of a full staple cartridge (154) that is properly seated may also prevent inadvertent and improper firing of end effector (116) on clamped tissue by cutting the tissue without also stapling the tissue, which could otherwise occur via transmission of distal motion from pusher member (166) to wedge sled (170). Each of the lockout mechanisms described below provides one or more of these functionalities.

A. First Exemplary Lockout Mechanism

Figure 12A:
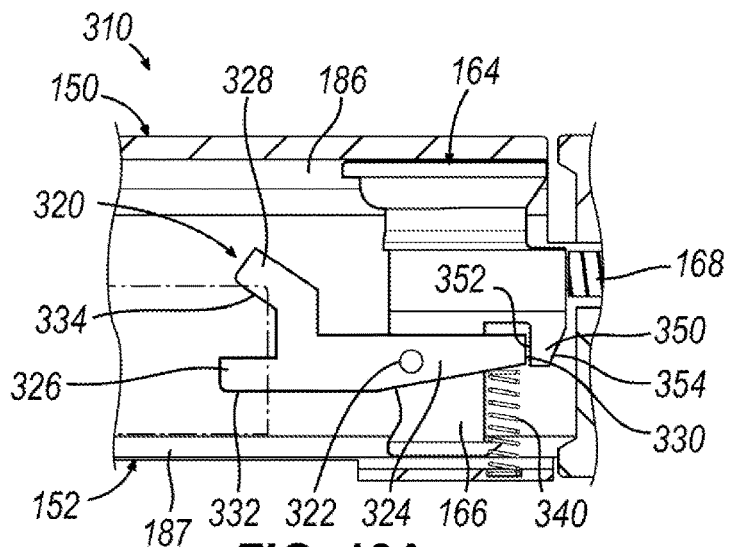
FIG. 12A depicts a side cross-sectional view of a proximal portion of another exemplary end effector for use with the robotic surgical system of FIG. 1, showing an exemplary lockout lever in a fully locked state for preventing firing of the end effector in the absence of a staple cartridge.
Figure 12B:
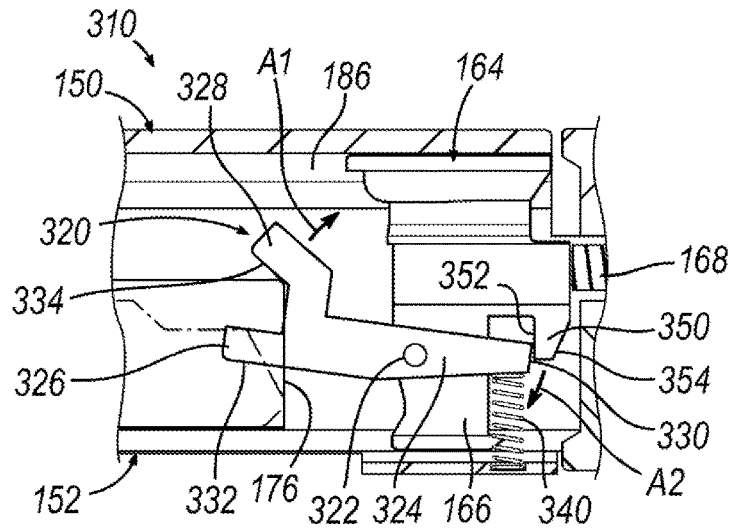
FIG. 12B depicts a side cross-sectional view of the proximal portion of the end effector of FIG. 12A, showing the lockout lever rotated to a partially locked state for preventing firing of the end effector with a spent staple cartridge.
Figure 12C:
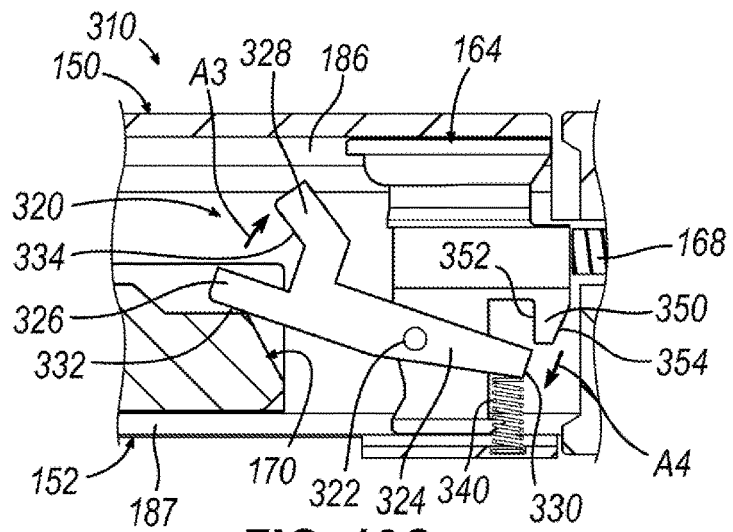
FIG. 12C depicts a side cross-sectional view of the proximal portion of the end effector of FIG. 12A, showing the lockout lever rotated to an unlocked state for allowing firing of the end effector with a full staple cartridge.

FIGS. 12A-12C show a proximal portion of an exemplary end effector (310) for use with surgical instrument (110) described above. End effector (310) is similar to end effector (116) described above except as otherwise described below. In this regard, end effector (310) includes upper and lower jaws (150, 152) and driving assembly (164) having pusher member (166) operatively coupled with an actuation mechanism (not shown), such as moveable member (128), via push rod (168).

As shown in FIGS. 12A-12C, end effector (310) includes at least a portion of a lockout mechanism that includes a lockout lever (320) pivotably coupled to the channel of lower jaw (152) via a pivot pin (322). For example, pivot pin (322) may pivotably couple lockout lever (320) to a sidewall (not shown) of the channel of lower jaw (152), such that lockout lever (320) is positioned laterally inwardly relative to the sidewall and thus within the channel. In the example shown, lockout lever (320) includes a proximal longitudinal portion (324), a lower distal prong portion (326) extending distally from a lower region of proximal longitudinal portion (324), and an upper distal prong portion (328) extending upwardly and distally from an upper region of proximal longitudinal portion (324), such that lockout lever (320) has a generally Y-shaped profile. In the example shown, pivot pin (322) is received within a bore provided in an intermediate region of proximal longitudinal portion (324).

As shown, a proximal end of proximal longitudinal portion (324) defines an output surface (330), a bottom of lower distal prong portion (326) defines a lower input surface (332), and a bottom of upper distal prong portion (328) defines an upper input surface (334), the purposes of which are described below. In some versions, output surface (330) may be at least partially defined by a proximal end of a detent (not shown) extending laterally inwardly from a proximal region of proximal longitudinal portion (324). At least a portion of lockout lever (320), such as lower distal prong portion (326), may be spaced apart from the laterally inner surface of the sidewall to which lockout lever (320) is pivotably coupled by a clearance gap sufficiently sized to accommodate a laterally outer sidewall of staple cartridge (154). In this manner, lower distal prong portion (326) may be configured to extend distally through proximal end (176) into an interior of staple cartridge (154) for accessing wedge sled (170) when staple cartridge (154) is installed within the channel of lower jaw (152), as described in greater detail below. In addition, or alternatively, at least lower and upper distal prong portions (326, 328), may be positioned laterally outwardly relative to pusher member (166) to avoid interfering with distal actuation of pusher member (166).

With continuing reference to FIGS. 12A-12C, lockout lever (320) is pivotable relative to the channel of lower jaw (152) about a fulcrum defined by pivot pin (322) between a fully locked state (FIG. 12A), a partially locked state (FIG. 12B), and an unlocked state (FIG. 12C). More particularly, lockout lever (320) of the present version is configured to be pivoted in a clockwise direction from the fully locked state toward the partially locked state, and is further configured to be pivoted in the clockwise direction from the partially locked state toward the unlocked state. In the example shown, lockout lever (320) is resiliently biased toward the fully locked state via a compression spring (340) positioned proximally of pivot pin (322) and extending between a bottom of proximal longitudinal portion (324) and a floor of the channel of lower jaw (152). It will be appreciated that lockout lever (320) may be resiliently biased toward the fully locked state in any other suitable manner, such as via a suitably-positioned tension spring, torsion spring, or any other suitable biasing member.

As best shown in FIG. 12B, upper input surface (334) is configured to be cammingly engaged by a portion of staple cartridge (154), such as proximal end (176), when staple cartridge (154) is installed within the channel of lower jaw (152) for urging lockout lever (320) from the fully locked state to the partially locked state. In this regard, upper input surface (334) may be positioned at a predetermined location and/or oriented at a predetermined angle selected to provide a desired camming engagement with proximal end (176) of staple cartridge (154) for urging lockout lever (320) from the fully locked state to the partially locked state. In some versions, upper input surface (334) may be configured to only provide the desired camming engagement with compatible staple cartridges having a predetermined size and/or geometry. For example, compatible staple cartridges may have substantially the same size and/or geometry as that of staple cartridge (154) (e.g., at least the proximal portion thereof), such that upper input surface (334) may not be capable of providing the desired camming engagement with incompatible staple cartridges having substantially different sizes and/or geometries from those of staple cartridge (154). In this manner, lockout lever (320) may be configured to remain in the fully locked state when an incompatible staple cartridge is installed within the channel of lower jaw (152). Likewise, lockout lever (320) may be configured to remain in the fully locked state when no staple cartridge is installed within the channel of lower jaw (152). It will be appreciated that a compatible staple cartridge is shown in phantom lines in FIG. 12A to illustrate the absence of such a compatible staple cartridge from lower jaw (152).

As best shown in FIG. 12C, lower input surface (332) is configured to be cammingly engaged by a portion of wedge sled (170), such as a proximal portion thereof, when staple cartridge (154) is installed within the channel of lower jaw (152) with wedge sled (170) in its initial proximal position for urging lockout lever (320) from the fully and/or partially locked state to the unlocked state. In this regard, lower input surface (332) may be positioned at a predetermined location and/or oriented at a predetermined angle selected to provide a desired camming engagement with the proximal portion of wedge sled (170) when wedge sled (170) is in its initial proximal position for urging lockout lever (320) from the fully and/or partially locked state to the unlocked state. In some versions, lower input surface (332) may be configured to only provide the desired camming engagement with compatible wedge sleds having a predetermined size and/or geometry. For example, compatible wedge sleds may have substantially the same size and/or geometry as that of wedge sled (170) (e.g., at least the proximal portion thereof), such that lower input surface (332) may not be capable of providing the desired camming engagement with incompatible wedge sleds having substantially different sizes and/or geometries from those of wedge sled (170). In this manner, lockout lever (320) may be configured to remain in the fully and/or partially locked state when a staple cartridge having an incompatible wedge sled is installed within the channel of lower jaw (152). It will be appreciated that a compatible wedge sled is shown in phantom lines in FIG. 12B to illustrate the absence of such a compatible wedge sled from staple cartridge (154).

In addition or alternatively, lower input surface (332) may be configured to only provide the desired camming engagement with the proximal portion of wedge sled (170) after upper input surface (334) has been cammingly engaged by proximal end (176) of staple cartridge (154) for urging lockout lever (320) from the fully locked state toward the partially locked state, such that lower input surface (332) may not be capable of providing the desired camming engagement with the proximal portion of wedge sled (170) when lockout lever (320) is in the fully locked state. In this manner, lockout lever (320) may be configured to remain in the fully locked state when an incompatible staple cartridge having wedge sled (170) is installed within the channel of lower jaw (152). Likewise, lockout lever (320) may be configured to remain in the partially locked state when staple cartridge (154) having an incompatible wedge sled is installed within the channel of lower jaw (152). Lockout lever (320) may also be configured to remain in the partially locked state when staple cartridge (154) having wedge sled (170) is installed within the channel of lower jaw (152) with wedge sled (170) located distally of its initial proximal position.

In the present version, the lockout mechanism also includes a stop detent (350) fixedly coupled to pusher member (166) and extending downwardly and/or laterally outwardly therefrom. As shown, a distal end of stop detent (350) defines a vertical catch surface (352) and a proximal end of stop detent (350) defines a ramp surface (354) tapered distally in a downward direction. Catch surface (352) is configured to be proximal of and selectively aligned with output surface (330) of lockout lever (320) in the longitudinal direction for selectively confronting and/or contacting output surface (330) when pusher member (166) is at an initial proximal position.

In this regard, output surface (330) is configured to be substantially entirely aligned with catch surface (352) in the longitudinal direction when pusher member (166) is at its initial proximal position with lockout lever (320) in the fully locked state, such that output surface (330) is substantially parallel to catch surface (352) and such that a substantial entirety of output surface (330) confronts and/or contacts catch surface (352) as shown in FIG. 12A. For example, output surface (330) may be positioned at a substantially same height as that of catch surface (352) relative to the floor of lower jaw (152). Thus, output surface (330) may fully abut or otherwise engage catch surface (352) to restrict distal movement of catch surface (352) together with pusher member (166). In this manner, output surface (330) and catch surface (352) may be configured to cooperate with each other to inhibit distal actuation of pusher member (166) when pusher member (166) is at its initial proximal position with lockout lever (320) in the fully locked state.

Output surface (330) is also configured to be partially aligned with catch surface (352) in the longitudinal direction when pusher member (166) is at its initial proximal position with lockout lever (320) in the partially locked state, such that output surface (330) is obliquely oriented relative to catch surface (352) and such that an upper portion of output surface (330) confronts and/or contacts catch surface (352) as shown in FIG. 12B. For example, the upper portion of output surface (330) may be positioned at a substantially same height as that of catch surface (352) relative to the floor of lower jaw (152). Thus, output surface (330) may partially abut or otherwise engage catch surface (352) to restrict distal movement of catch surface (352) together with pusher member (166). In this manner, output surface (330) and catch surface (352) may be configured to cooperate with each other to inhibit distal actuation of pusher member (166) when pusher member (166) is at its initial proximal position with lockout lever (320) in the partially locked state.

Output surface (330) is further configured to be offset from catch surface (352) in the longitudinal direction when pusher member (166) is at its initial proximal position with lockout lever (320) in the unlocked state, such that output surface (330) is obliquely oriented relative to catch surface (352) and such that no portion of output surface (330) confronts and/or contacts catch surface (352) as shown in FIG. 12C. For example, output surface (330) may be positioned at a substantially lower height than that of catch surface (352) relative to the floor of lower jaw (152). Thus, output surface (330) may be fully disengaged from catch surface (352) to permit distal movement of catch surface (352) together with pusher member (166). In this manner, output surface (330) and catch surface (352) may be configured to disengage from each other to permit distal actuation of pusher member (166) when pusher member (166) is at its initial proximal position with lockout lever (320) in the unlocked state.

During operation, lockout lever (320) may initially be in the fully locked state when staple cartridge (154) is absent from lower jaw (152), as shown in FIG. 12A, such that output surface (330) fully engages catch surface (352). A closing and/or firing of end effector (310) in the absence of staple cartridge (154) may then be initiated, such as by transmitting distal motion to pusher member (166) from moveable member (128) via push rod (168). However, distal actuation of pusher member (166) may be inhibited by the engagement between output surface (330) and catch surface (352), thereby preventing the closing and/or firing from being completed.

A spent staple cartridge (154) (e.g., with wedge sled (170) either absent or located distally of its initial proximal position) may subsequently be installed within lower jaw (152), thereby allowing proximal end (176) of staple cartridge (154) to cammingly engage upper input surface (334), as indicated by arrow (A1) in FIG. 12B, such that output surface (330) partially disengages catch surface (352), as indicated by arrow (A2) in FIG. 12B. A closing and/or firing of end effector (310) with spent staple cartridge (154) may then be initiated, such as by transmitting distal motion to pusher member (166) from moveable member (128) via push rod (168). However, distal actuation of pusher member (166) may continue to be inhibited by the partial engagement between output surface (330) and catch surface (352), thereby preventing the firing from being completed. In some versions, slight distal actuation of pusher member (166) may be permitted by the partial disengagement of output surface (330) from catch surface (352), thereby allowing the closing to be completed.

A full staple cartridge (154) (e.g., with wedge sled (170) at its initial proximal position) may then be installed within lower jaw (152), thereby allowing the proximal portion of wedge sled (170) to cammingly engage lower input surface (332), as indicated by arrow (A3) in FIG. 12C, such that output surface (330) fully disengages catch surface (352), as indicated by arrow (A4) in FIG. 12C. A closing and/or firing of end effector (310) with full staple cartridge (154) may then be initiated, such as by transmitting distal motion to pusher member (166) from moveable member (128) via push rod (168). In this regard, distal actuation of pusher member (166) may be permitted by the disengagement of output surface (330) from catch surface (352), thereby allowing the closing and/or firing to be completed.

It will be appreciated that during firing of end effector (310), wedge sled (170) is advanced distally via the distal actuation of pusher member (166) such that the proximal portion of wedge sled (170) disengages lower input surface (332). Due to the resilient biasing of lockout lever (320) toward its fully locked state via compression spring (340), lockout lever (320) may then automatically return to its partially locked state in which proximal end (176) of staple cartridge (154) engages upper input surface (334). In instances where pusher member (166) is retracted to its initial proximal position after firing while spent staple cartridge (154) remains installed within lower jaw (152), output surface (330) may resume partially engaging catch surface (352), thereby preventing further firing of end effector (310) with spent staple cartridge (154). In some versions, further closing of end effector (310) with spent staple cartridge (154) may be permitted. In any event, spent staple cartridge (154) may be removed from lower jaw (152) after firing such that proximal end (176) of staple cartridge (154) disengages upper input surface (334). Due to the resilient biasing of lockout lever (320) toward its fully locked state via compression spring (340), lockout lever (320) may then automatically return to its fully locked state. In instances where pusher member (166) is retracted to its initial proximal position after firing, output surface (330) may resume fully engaging catch surface (352), thereby preventing further closing and/or firing of end effector (310) in the absence of staple cartridge (154).

In some versions, when pusher member (166) is retracted toward its initial proximal position after firing, the ramp surface (354) of detent (350) may cammingly engage a portion of lockout lever (320) (e.g., a distal end of a laterally-inwardly extending detent whose proximal end at least partially defines output surface (330)) to thereby urge lockout lever (320) from the fully and/or partially locked state toward the unlocked state to permit retraction of pusher member (166) to its initial proximal position. In this regard, ramp surface (354) may be oriented at a predetermined angle selected to provide a desired camming engagement with such a portion of lockout lever (320) for urging lockout lever (320) from the fully and/or partially locked state toward the unlocked state.

B. Second Exemplary Lockout Mechanism

Figure 13A:
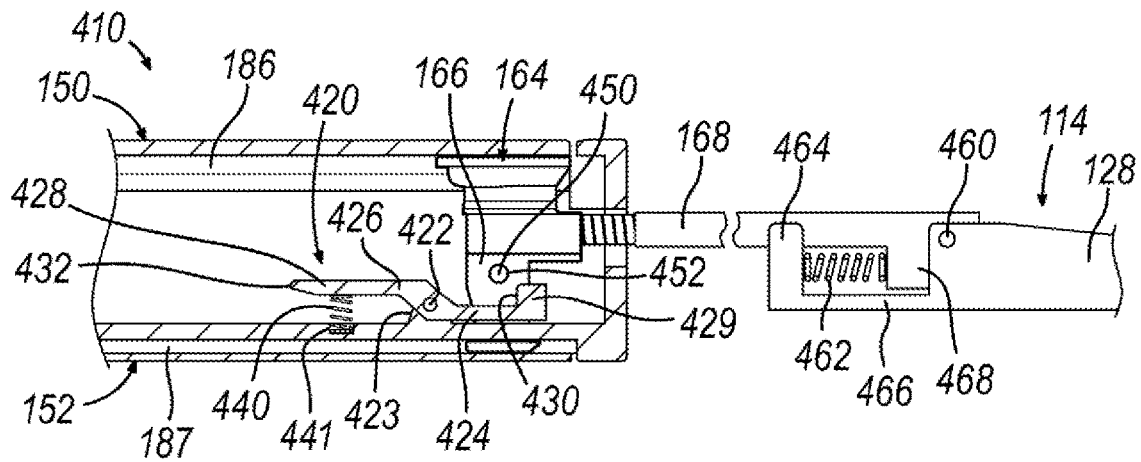
FIG. 13A depicts a side cross-sectional view of a proximal portion of another exemplary end effector for use with the robotic surgical system of FIG. 1, showing another exemplary lockout lever in an unlatched state for permitting proximal pulling of the pusher member shown in FIG. 8, and further showing the moveable member shown in FIG. 8 in a disengaged state for preventing firing of the end effector in the absence of a full staple cartridge.
Figure 13B:
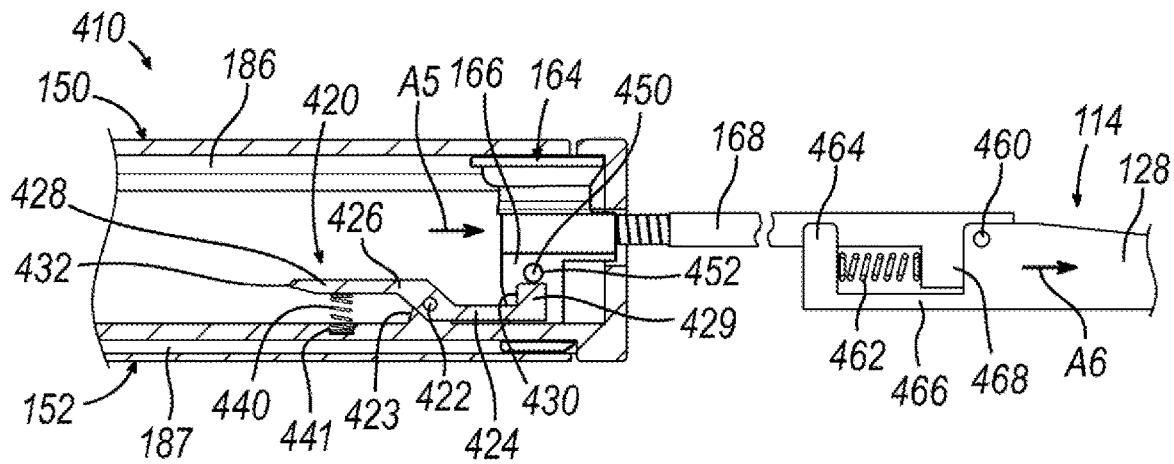
FIG. 13B depicts a side cross-sectional view of the proximal portion of the end effector of FIG. 13A, showing the lockout lever in the unlatched state, and further showing the moveable member translated proximally together with the pusher member to remain in the disengaged state for preventing firing of the end effector in the absence of a full staple cartridge.
Figure 13C:
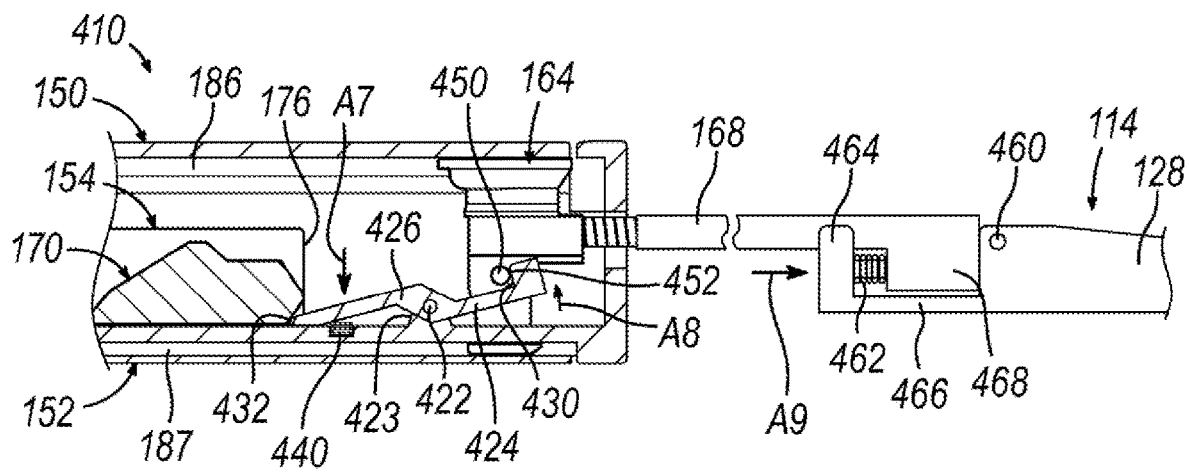
FIG. 13C depicts a side cross-sectional view of the proximal portion of the end effector of FIG. 13A, showing the lockout lever in a latched state for restricting proximal pulling of the pusher member, and further showing the moveable member translated proximally relative to the pusher member to an engaged state for allowing firing of the end effector with a full staple cartridge.
Figure 14:
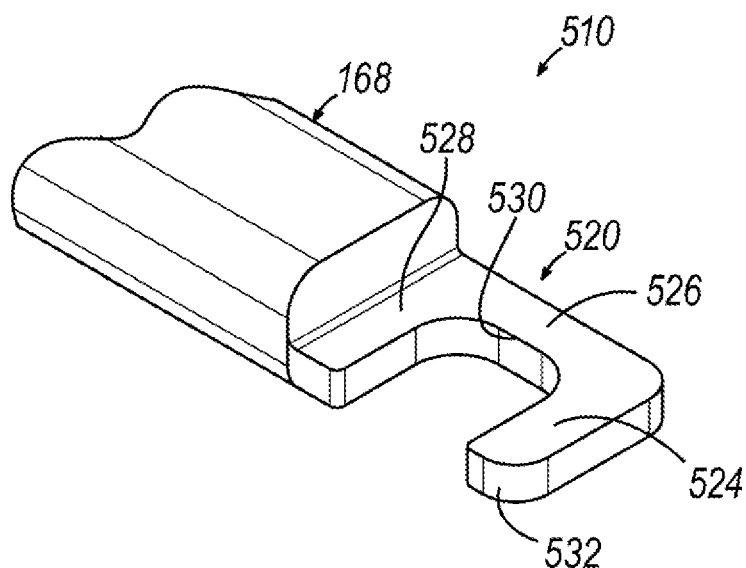
FIG. 14 depicts a perspective view of a proximal portion of another exemplary end effector for use with the robotic surgical system of FIG. 1, showing a lockout hook attached to the proximal end of the push rod shown in FIG. 8.

FIGS. 13A-13C show a proximal portion of another exemplary end effector (410) for use with surgical instrument (110) described above, and further show a distal portion of shaft assembly (114) of surgical instrument (110) including moveable feature (128). End effector (410) is similar to end effector (116) described above except as otherwise described below. In this regard, end effector (410) includes upper and lower jaws (150, 152) and driving assembly (164) having pusher member (166) configured to be selectively operatively coupled with moveable feature (128) via push rod (168).

As shown in FIGS. 13A-13C, end effector (410) includes at least a portion of a lockout mechanism that includes a lockout lever (420) pivotably coupled to the channel of lower jaw (152) via a pivot pin (422). For example, pivot pin (422) may pivotably couple lockout lever (420) to a pivot block (423) extending upwardly from a floor of the channel of lower jaw (152), such that lockout lever (420) is positioned within the channel. In the example shown, lockout lever (420) includes a proximal longitudinal portion (424), an intermediate angled portion (426) extending upwardly and distally from a distal end of proximal longitudinal portion (424), and a distal longitudinal portion (428) extending distally from a distal end of intermediate angled portion (426), such that lockout lever (420) has a generally Z-shaped profile. In the example shown, pivot pin (422) is received within a bore provided in intermediate angled portion (426). Lockout lever (420) of the present version further includes a detent (429) extending upwardly and/or laterally inwardly from a proximal region of proximal longitudinal portion (424).

As shown, a distal end of detent (429) defines an output surface (430) and a distal end of distal longitudinal portion (428) defines an input surface (432), the purposes of which are described below. At least a portion of lockout lever (420), such as distal longitudinal portion (428), may be spaced apart from the laterally inner surface of an adjacent sidewall of the channel of lower jaw (152) by a clearance gap sufficiently sized to accommodate a laterally outer sidewall of staple cartridge (154). In this manner, distal longitudinal portion (428) may be configured to extend distally through proximal end (176) into an interior of staple cartridge (154) for accessing wedge sled (170) when staple cartridge (154) is installed within the channel of lower jaw (152), as described in greater detail below. In addition, or alternatively, any one or more of proximal longitudinal portion (424), intermediate angled portion (426), and/or distal longitudinal portion (428) may be positioned laterally outwardly relative to pusher member (166) to avoid interfering with distal actuation of pusher member (166).

With continuing reference to FIGS. 13A-13C, lockout lever (420) is pivotable relative to the channel of lower jaw (152) about a fulcrum defined by pivot pin (422) between an unlatched state (FIGS. 13A and 13B) and a latched state (FIG. 13C). More particularly, lockout lever (420) of the present version is configured to be pivoted in a counterclockwise direction from the unlatched state toward the latched state. In the example shown, lockout lever (420) is resiliently biased toward the unlatched state via a compression spring (440) positioned distally of pivot pin (422) and extending between a bottom of distal longitudinal portion (428) and a recess (441) provided in the floor of the channel of lower jaw (152). It will be appreciated that lockout lever (420) may be resiliently biased toward the unlatched state in any other suitable manner, such as via a suitably-positioned tension spring, torsion spring, or any other suitable biasing member.

As best shown in FIG. 13C, input surface (432) is configured to be cammingly engaged by a portion of wedge sled (170), such as a proximal portion thereof, when staple cartridge (154) is installed within the channel of lower jaw (152) with wedge sled (170) in its initial proximal position for urging lockout lever (420) from the unlatched state to the latched state. In this regard, input surface (432) may be positioned at a predetermined location and/or oriented at a predetermined angle selected to provide a desired camming engagement with the proximal portion of wedge sled (170) when wedge sled (170) is in its initial proximal position for urging lockout lever (420) from the unlatched state to the latched state. In some versions, input surface (432) may be configured to only provide the desired camming engagement with compatible wedge sleds having a predetermined size and/or geometry. For example, compatible wedge sleds may have substantially the same size and/or geometry as that of wedge sled (170) (e.g. at least the proximal portion thereof), such that input surface (432) may not be capable of providing the desired camming engagement with incompatible wedge sleds having substantially different sizes and/or geometries from those of wedge sled (170). In this manner, lockout lever (420) may be configured to remain in the unlatched state when a staple cartridge having an incompatible wedge sled is installed within the channel of lower jaw (152). Likewise, lockout lever (420) may be configured to remain in the unlatched state when staple cartridge (154) having wedge sled (170) is installed within the channel of lower jaw (152) with wedge sled (170) located distally of its initial proximal position.

In the present version, the lockout mechanism also includes a stop pin (450) fixedly coupled to pusher member (166) and extending laterally outwardly therefrom. As shown, a proximal end of stop pin (450) defines a semicircular catch surface (452). Catch surface (452) is configured to be distal of and selectively aligned with output surface (430) of lockout lever (420) in the longitudinal direction for selectively confronting and/or contacting output surface (430) when pusher member (166) is at an initial proximal position.

In this regard, output surface (430) is configured to be at least partially aligned with catch surface (452) in the longitudinal direction when pusher member (166) is at its initial proximal position with lockout lever (320) in the latched state, such that at least a portion of output surface (430) confronts and/or contacts catch surface (452) as shown in FIG. 13C. For example, output surface (430) may be positioned at a substantially same height as that of catch surface (452) relative to the floor of lower jaw (152). Thus, output surface (430) may at least partially abut or otherwise engage catch surface (452) to restrict proximal movement of catch surface (452) together with pusher member (166). In this manner, output surface (430) and catch surface (452) may be configured to cooperate with each other to inhibit proximal pulling of pusher member (166) when pusher member (166) is at its initial proximal position with lockout lever (420) in the latched state.

Output surface (430) is further configured to be offset from catch surface (452) in the longitudinal direction when pusher member (166) is at its initial proximal position with lockout lever (420) in the unlatched state, such that no portion of output surface (430) confronts and/or contacts catch surface (452) as shown in FIGS. 13A and 13B. For example, output surface (430) may be positioned at a substantially lower height than that of catch surface (452) relative to the floor of lower jaw (152). Thus, output surface (430) may be fully disengaged from catch surface (452) to permit proximal movement of catch surface (452) together with pusher member (166). In this manner, output surface (430) and catch surface (452) may be configured to disengage from each other to permit proximal pulling of pusher member (166) when pusher member (166) is at its initial proximal position with lockout lever (420) in the unlatched state.

In the present version, the lockout mechanism further includes at least one transmission member in the form of a laterally-opposed pair of spring-loaded push pins (460) (one shown) positioned at a distal region of moveable feature (128). Each push pin (460) is configured to move in the lateral direction between a retracted state in which push pin (460) is substantially housed within moveable feature (128) and an extended state in which push pin (460) protrudes from moveable feature (128) in the lateral direction (e.g., laterally inwardly). Push pins (460) may be resiliently biased toward the respective extended states by any suitable biasing member(s).

With continuing reference to FIGS. 13A-13C, moveable feature (128) is translatable relative to push rod (168) between a disengaged state (FIGS. 13A and 13B) and an engaged state (FIG. 13C). More particularly, moveable feature (128) of the present version is configured to be translated distally from the disengaged state toward the engaged state. In the example shown, moveable feature (128) is resiliently biased distally relative to push rod (168) toward the disengaged state via a compression spring (462). In this regard, a distal ledge (464) is fixedly coupled to moveable feature (128) via a longitudinal support (466) extending between a lower, distal region of moveable feature (128) and a lower, proximal region of distal ledge (464). Compression spring (462) extends proximally from a proximal end of distal ledge (464) toward distal ends of a laterally-opposed pair of proximal flag(s) (468) (one shown) which extend downwardly and/or proximally from push rod (168). In some versions, proximal flag(s) (468) may extend downwardly from one or more respective band(s) extending proximally from push rod (168). It will be appreciated that moveable feature (128) may be resiliently biased toward the disengaged state in any other suitable manner, such as via a suitably-positioned tension spring or any other suitable biasing member.

Push pins (460) are configured to be offset from the corresponding flags (468) in the lateral direction when moveable feature (128) is in the engaged state, such that push pins (460) may resiliently return to their respective extended states as shown in FIG. 13C. For example, push pins (460) may each be positioned proximally of the corresponding flag (468). Thus, the distal ends of push pins (460) may at least partially abut or otherwise engage the proximal ends of the corresponding flags (468) to permit transmission of distal motion from push pins (460) to flags (468) and thereby operatively couple pusher member (166) with moveable feature (128). In this manner, push pins (460) and flags (468) may be configured to cooperate with each other to permit distal actuation of pusher member (166) when moveable feature (128) is in the engaged state.

Push pins (460) are further configured to be at least partially aligned with the corresponding flags (468) in the lateral direction when moveable feature (128) is in the disengaged state, such that push pins (460) may be urged toward their respective retracted states by the laterally outer surfaces of the corresponding flags (468) as shown in FIGS. 13A and 13B. For example, push pins (460) may each be positioned at a substantially same longitudinal position as that of at least a portion of the corresponding flag (468). Thus, the distal ends of push pins (460) may be distal of, and thus disengaged from, the proximal ends of the corresponding flags (468) to restrict transmission of distal motion from push pins (460) to flags (468) and thereby operatively decouple pusher member (166) from moveable feature (128). In this manner, push pins (460) and flags (468) may be configured to cooperate with each other to inhibit distal actuation of pusher member (166) when moveable feature (128) is in the disengaged state.

During operation, lockout lever (420) may initially be in the unlatched state and moveable feature (128) may initially be in the disengaged state when staple cartridge (154) is absent from lower jaw (152), as shown in FIG. 13A, such that output surface (430) is disengaged from catch surface (452) and such that push pins (460) engage the laterally outer surfaces of flags (468) and are thereby urged to their retracted states. A closing and/or firing of end effector (410) in the absence of staple cartridge (154) may then be initiated, such as by translating moveable feature (128) slightly proximally relative to end effector (410), as indicated by arrow (A5) in FIG. 13B, prior to translating moveable feature (128) distally for attempting distal actuation of pusher member (166). Such initial, slight proximal translation may detect whether a full staple cartridge (154) is installed within lower jaw (152). In this regard, proximal pulling of pusher member (166) from its initial proximal position by moveable feature (128) via compression spring (462) may be permitted by the disengagement of output surface (430) from catch surface (452), as indicated by arrow (A6) in FIG. 13B, to maintain moveable feature (128) in the disengaged state (e.g., with push pins (460) being translated slightly proximally together with the corresponding flags (468)), thereby maintaining push pins (460) in their retracted states such that the distal ends of push pins (460) remain disengaged from the proximal ends of flags (468). Thus, distal actuation of pusher member (166) may be inhibited by the disengagement of the distal ends of push pins (460) from the proximal ends of flags (468) resulting from the disengagement of output surface (430) from catch surface (452), thereby preventing the closing and/or firing from being completed. More particularly, distal translation of moveable feature (128) following the slight proximal translation of moveable feature (128) may be performed without transmitting sufficient distal motion from push pins (460) to flags (468) for achieving distal actuation of pusher member (166).

A full staple cartridge (154) (e.g., with wedge sled (170) at its initial proximal position) may then be installed within lower jaw (152), thereby allowing the proximal portion of wedge sled (170) to cammingly engage input surface (432), as indicated by arrow (A7) in FIG. 13C, such that output surface (430) engages catch surface (452), as indicated by arrow (A8) in FIG. 13C. A closing and/or firing of end effector (410) with full staple cartridge (154) may then be initiated, such as by translating moveable feature (128) slightly proximally relative to end effector (410) as described above and as indicated by arrow (A9) in FIG. 13C. In this regard, proximal pulling of pusher member (166) from its initial proximal position by moveable feature (128) via compression spring (462) may be restricted by the engagement of output surface (430) with catch surface (452) to allow moveable feature (128) to translate distally relative to push rod (168) toward the engaged state (e.g., with push pins (460) being translated slightly proximally relative to the corresponding flags (468)) while compressing compression spring (462), thereby allowing push pins (460) to resiliently return to their extended states such that the distal ends of push pins (460) engage the proximal ends of flags (468). Thus, distal actuation of pusher member (166) may be permitted by the engagement between push pins (460) and the proximal ends of flags (468) resulting from the engagement of output surface (430) with catch surface (452), thereby allowing the closing and/or firing to be completed. More particularly, distal translation of moveable feature (128) following the slight proximal translation of moveable feature (128) may be performed while transmitting sufficient distal motion from push pins (460) to flags (468) for achieving distal actuation of pusher member (166).

It will be appreciated that during firing of end effector (410), wedge sled (170) is advanced distally via the distal actuation of pusher member (166) such that the proximal portion of wedge sled (170) disengages input surface (432). Due to the resilient biasing of lockout lever (420) toward its unlatched state via compression spring (440), lockout lever (420) may then automatically return to its unlatched state. In instances where pusher member (166) is retracted to its initial proximal position after firing while spent staple cartridge (154) remains installed within lower jaw (152), output surface (430) may remain disengaged from catch surface (452), thereby preventing further closing and/or firing of end effector (410) with spent staple cartridge (154). In any event, spent staple cartridge (154) may be removed from lower jaw (152) after firing, such that output surface (430) may remain disengaged from catch surface (452), thereby preventing further closing and/or firing of end effector (410) in the absence of staple cartridge (154).

C. Third Exemplary Lockout Mechanism

FIGS. 14-17 show a proximal portion of another exemplary end effector (510) for use with surgical instrument (110) described above, and further show a distal portion of shaft assembly (114) of surgical instrument (110) including moveable feature (128), which is moveably housed within an outer tube (512). End effector (510) is similar to end effector (116) described above except as otherwise described below. In this regard, end effector (510) includes upper and lower jaws (not shown), such as upper and lower jaws (150, 152), and driving assembly (164) having a pusher member (not shown), such as pusher member (166), configured to be selectively operatively coupled with moveable feature (128) via push rod (168).

As shown in FIGS. 14, 15B, and 16-17, end effector (510) includes at least a portion of a lockout mechanism that includes a lockout hook (520) extending proximally from push rod (168). In some versions, lockout hook (520) may extend proximally from one or more bands extending proximally from push rod (168). In the example shown, lockout hook (520) includes a proximal lateral portion (524), an intermediate longitudinal portion (526) extending distally from a first lateral end of proximal lateral portion (524) to a lateral end of a distal lateral portion (528) coupled to push rod (168), such that lockout hook (520) has a generally C-shaped profile. As shown, proximal lateral portion (524), intermediate longitudinal portion (526), and distal lateral portion (528) collectively define a recess (530), the purpose of which is described below. In the present version, a proximal end of proximal lateral portion (524) defines a ramp surface (532) curved distally in a laterally-outward direction and positioned at or near a second lateral end of proximal lateral portion (524) opposite the first lateral end of proximal lateral portion (524).

With reference to FIGS. 15A-17, lockout hook (520) is translatable relative to outer tube (512) of shaft assembly (114) between an unavailable state in which recess (530) is distal of a predetermined pickup location (FIGS. 15A and 17) and an available state in which recess (530) is at the predetermined pickup location (FIGS. 15B and 16), as described in greater detail below. More particularly, lockout hook (520) of the present version is configured to be translated proximally from the unavailable state toward the available state. Lockout hook (520) may be resiliently biased toward the unavailable state via a suitably-positioned compression spring, tension spring, or any other suitable biasing member (not shown).

A portion of driving assembly (164), such as pusher member (166), may define an input surface (not shown) configured to be engaged by a portion of wedge sled (170), such as a proximal portion thereof, when staple cartridge (154) is installed within the channel of lower jaw (152) with wedge sled (170) in its initial proximal position for urging pusher member (166) slightly proximally from its initial proximal position, thereby urging lockout hook (520) from the unavailable state to the available state. In this regard, the input surface may be positioned at a predetermined location and/or oriented at a predetermined angle selected to provide a desired pushing engagement with the proximal portion of wedge sled (170) when wedge sled (170) is in its initial proximal position for urging lockout hook (520) from the unavailable state to the available state. In some versions, the input surface may be configured to only provide the desired pushing engagement with compatible wedge sleds having substantially the same size and/or geometry of wedge sled (170) (e.g. at least the proximal portion thereof), such that the input surface may not be capable of providing the desired pushing engagement with incompatible wedge sleds having substantially different sizes and/or geometries from those of wedge sled (170). In this manner, lockout hook (520) may be configured to remain in the unavailable state when a staple cartridge having an incompatible wedge sled is installed within the channel of lower jaw (152). Likewise, lockout hook (520) may be configured to remain in the unavailable state when staple cartridge (154) having wedge sled (170) is installed within the channel of lower jaw (152) with wedge sled (170) located distally of its initial proximal position.

In the present version, the lockout mechanism also includes at least one transmission member in the form of a detent (560) extending in a first radial direction (e.g., laterally or transversely) from a longitudinal support (566) which extends distally from moveable feature (128). A tooth (570) extends from moveable feature (128) in a second radial direction perpendicular to the first radial direction. For example, detent (560) may extend one of laterally or transversely from longitudinal support (566) and tooth (570) may extend the other of laterally or transversely from moveable feature (128), as described in greater detail below.

Figure 15A:
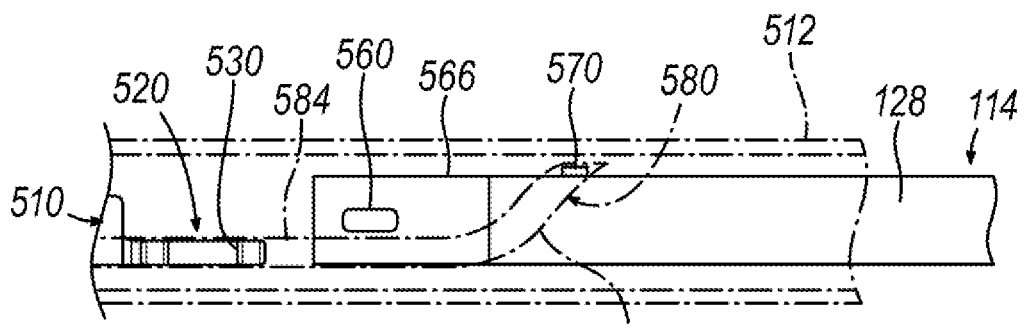
FIG. 15A depicts a side elevation view of the proximal portion of the end effector of FIG. 14, showing the lockout hook in an unavailable state, and further showing the moveable member shown in FIG. 8 in a proximal state.
Figure 15B:
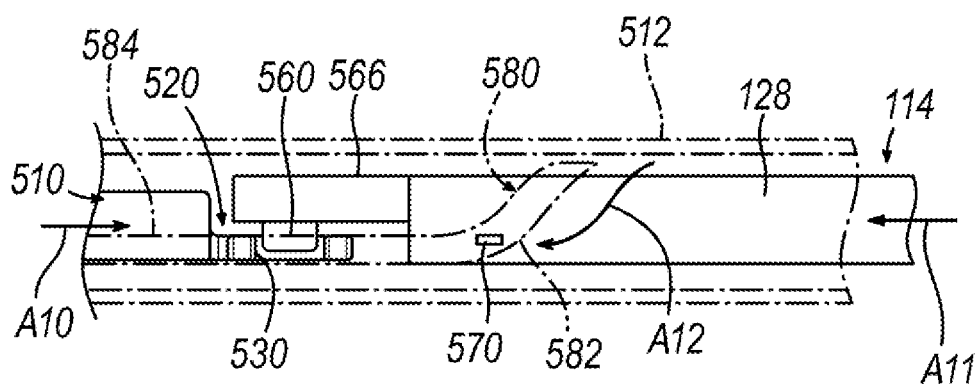
FIG. 15B depicts a side elevation view of the proximal portion of the end effector of FIG. 14, showing the lockout hook in an available state, and further showing the moveable member in an intermediate state.

With continuing reference to FIGS. 15A-15B, moveable feature (128) is twistable relative to outer tube (512) between a proximal state (FIG. 15A) and an intermediate state (FIG. 15B), and is translatable relative to outer tube (512) between the intermediate state and a distal state (not shown). More particularly, moveable feature (128) of the present version is configured to be twisted counterclockwise and distally from the proximal state toward the intermediate state, and to be translated distally from the intermediate state to the distal state. In this regard, outer tube (512) includes a groove (also referred to as a thread) (580) extending radially outwardly from a radially inner surface of outer tube (512) and configured to slidably receive tooth (570) for guiding movement of moveable feature (128) relative to outer tube (512). In the example shown, groove (580) includes a proximal quarter-helical groove portion (582) for guiding twisting of moveable feature (128) relative to outer tube (512) and a distal longitudinal groove portion (584) for guiding translation of moveable feature (128) relative to outer tube (512). Proximal quarter-helical groove portion (582) is configured to guide tooth (570) from a first orientation about the longitudinal axis in which tooth (570) extends transversely from moveable feature (128) such that detent (560) extends laterally from longitudinal support (566) proximal of the predetermined pickup location when moveable feature (128) is in the proximal state (FIG. 15A) to a second orientation about the longitudinal axis in which tooth (570) extends laterally from moveable feature (128) such that detent (560) extends transversely from longitudinal support (566) at the predetermined pickup location when moveable feature (128) is in the intermediate state (FIG. 15B). Distal longitudinal groove portion (584) is configured to maintain tooth (570) in the second orientation such that tooth (570) continues extending laterally from moveable feature (128) and detent (560) continues extending transversely from longitudinal support (566) when moveable feature is between the intermediate and distal states. In this manner, tooth (570) and groove (580) may be configured to cooperate with each other to reorient detent (560) about the longitudinal axis during twisting of moveable feature (128) from the proximal state to the intermediate state, and to maintain the orientation of detent (560) about the longitudinal axis during translation of moveable feature (128) from the intermediate state to the distal state. Moveable feature (128) may be resiliently biased toward the proximal state via a suitably-positioned compression spring, tension spring, torsion spring, or any other suitable biasing member (not shown).

Figure 16:
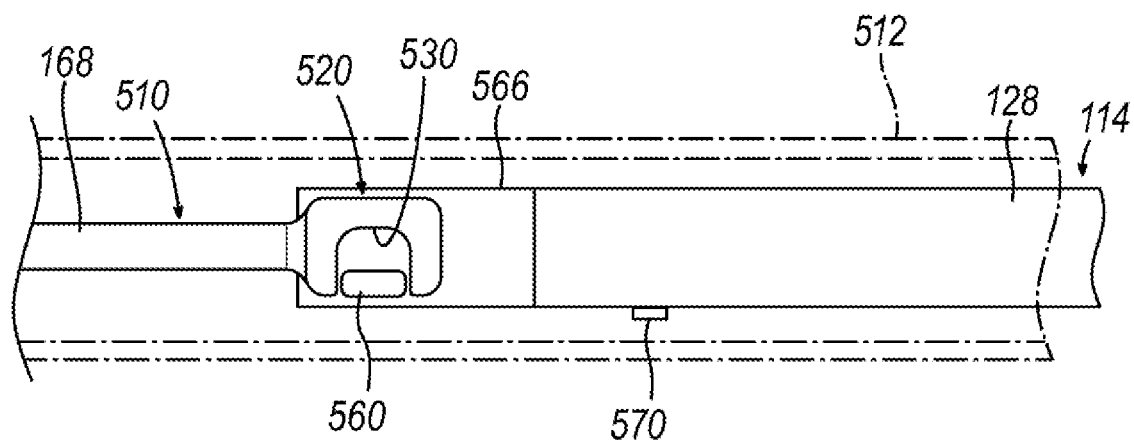
FIG. 16 depicts a bottom view of the proximal portion of the end effector of FIG. 14, showing the lockout hook in the available state, and further showing the moveable member in the intermediate state.

Detent (560) is configured to be at least partially aligned with recess (530) in the transverse direction when moveable feature (128) is in the intermediate state with lockout hook (520) in the available state, such that detent (560) may be received within recess (530) as shown in FIGS. 15B and 16. For example, detent (560) and recess (530) may each be positioned at the predetermined pickup location. Thus, the distal end of detent (560) may at least partially abut or otherwise engage the distal end of recess (530) to permit transmission of distal motion from detent (560) to recess (530) and thereby operatively couple pusher member (166) with moveable feature (128). In this manner, detent (560) and recess (530) may be configured to cooperate with each other to permit distal actuation of pusher member (166) when moveable feature (128) is in the intermediate state with lockout hook (520) in the available state.

Figure 17:
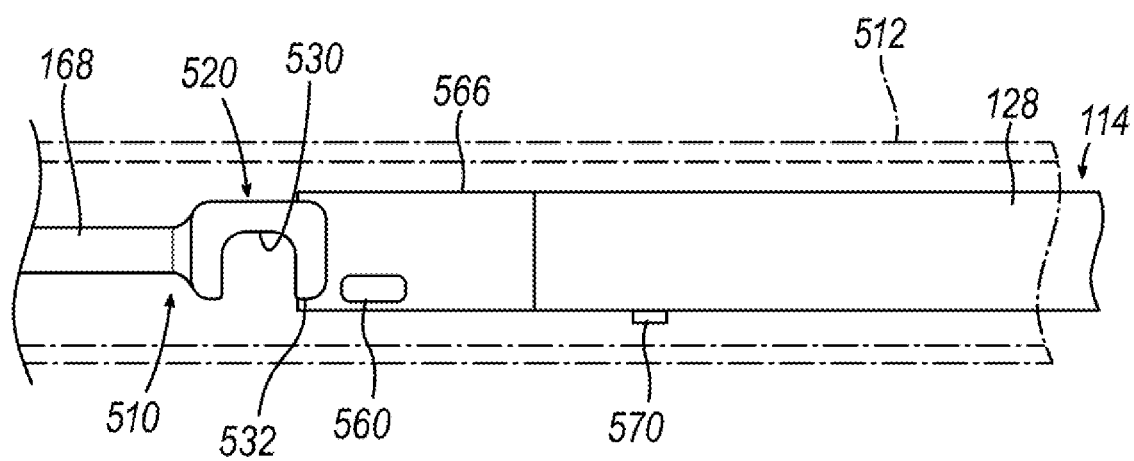
FIG. 17 depicts a bottom view of the proximal portion of the end effector of FIG. 14, showing the lockout hook in the unavailable state, and further showing the moveable member in the intermediate state.

Detent (560) is further configured to be offset from recess (530) in the transverse direction when moveable feature (128) is in the intermediate state with lockout hook (520) in the unavailable state, such that detent (560) may be positioned outside of recess (530) as shown in FIG. 17. For example, detent (560) may be positioned at the predetermined pickup location while recess (530) may be positioned distal of the predetermined pickup location such that the distal end of detent (560) is disengaged from the distal end of recess (530). In some versions, detent (560) may be configured to cammingly engage ramp surface (532) of lockout hook (520) to thereby urge lockout hook (520) laterally away from detent (560) and thereby permit detent (560) to bypass recess (530) distally without being received therein, such that the distal end of detent (560) remains disengaged from the distal end of recess (540) to restrict transmission of distal motion from detent (560) to recess (530) and thereby operatively decouple pusher member (166) from moveable feature (128). In this manner, detent (560) and recess (530) may be configured to cooperate with each other to inhibit distal actuation of pusher member (166) when moveable feature (128) is in the intermediate state with lockout hook (520) in the unavailable state.

During operation, lockout hook (520) may initially be in the unavailable state in which recess (530) is distal of the predetermined pickup location and moveable feature (128) may initially be in the proximal state when staple cartridge (154) is absent from lower jaw (152), as shown in FIG. 15A, such that detent (560) is positioned outside of recess (530) with the distal end of detent (560) disengaged from the distal end of recess (530). A closing and/or firing of end effector (510) in the absence of staple cartridge (154) may then be initiated, such as by transmitting distal motion to moveable member (128) via portions of drive train (126), thereby twisting moveable feature from the proximal state to the intermediate state as proximal quarter-helical groove portion (582) guides tooth (570) from the first orientation to the second orientation for reorienting detent (560) to extend transversely from longitudinal support (566) at the predetermined pickup location, as shown in FIG. 17. However, detent (560) may remain outside of recess (530) such that the distal end of detent (560) remains disengaged from the distal end of recess (530). Thus, distal actuation of pusher member (166) may be inhibited by the disengagement of the distal end of detent (560) from the distal end of recess (530), thereby preventing the closing and/or firing from being completed. More particularly, distal translation of moveable feature (128) from the intermediate state to the distal state may be performed without transmitting sufficient distal motion from detent (560) to recess (530) for achieving distal actuation of pusher member (166). In this regard, detent (560) may cammingly engage ramp surface (532) of lockout hook (520) during distal translation of moveable feature (128) toward the distal state as described above to permit detent (560) to bypass recess (530) distally without being received therein.

A full staple cartridge (154) (e.g., with wedge sled (170) at its initial proximal position) may then be installed within lower jaw (152), thereby allowing the proximal portion of wedge sled (170) to push the input surface of pusher member (166) for urging lockout hook (520) from the unavailable state to the available state in which recess (530) is at the predetermined pickup location, as indicated by arrow (A10) in FIG. 15B. A closing and/or firing of end effector (510) with full staple cartridge (154) may then be initiated, such as by transmitting distal motion to moveable member (128) via one or more portions of drive train (126), as indicated by arrow (A11) in FIG. 15B, thereby twisting moveable feature from the proximal state to the intermediate state as proximal quarter-helical groove portion (582) guides tooth (570) from the first orientation to the second orientation for reorienting detent (560) to extend transversely from longitudinal support (566) at the predetermined pickup location, as indicated by arrow (A12) in FIG. 15B. In this regard, detent (560) may be received within recess (530) at the predetermined pickup location such that the distal end of detent (560) engages the distal end of recess (530), as shown in FIG. 16. Thus, distal actuation of pusher member (166) may be permitted by the engagement of the distal end of detent (560) with the distal end of recess (530), thereby allowing the closing and/or firing to be completed. More particularly, distal translation of moveable feature (128) from the intermediate state to the distal state may be performed while transmitting sufficient distal motion from detent (560) to recess (530) for achieving distal actuation of pusher member (166).

It will be appreciated that during firing of end effector (510), wedge sled (170) is advanced distally via the distal actuation of pusher member (166), such that the proximal portion of wedge sled (170) may disengage the input surface of pusher member (166) upon retraction of pusher member (166) to its initial proximal position. In some versions, retraction of pusher member (166) may be achieved by translating moveable feature (128) from the distal state to the intermediate state via engagement of the proximal end of detent (560) with the proximal end of recess (530), such that lockout hook (520) may be returned to the available state. Twisting moveable feature (128) from the intermediate state to the proximal state may then remove detent (560) from recess (530) such that the proximal end of detent (560) may disengage the proximal end of recess (530). Due to the resilient biasing of lockout hook (520) toward its unavailable state, lockout hook (520) may then automatically return to its unavailable state in which recess (530) is distal of the predetermined pickup location. In instances where pusher member (166) is retracted to its initial proximal position after firing while spent staple cartridge (154) remains installed within lower jaw (152), the proximal portion of wedge sled (170) may remain disengaged from the input surface of pusher member (166), thereby preventing further closing and/or firing of end effector (510) with spent staple cartridge (154). In any event, spent staple cartridge (154) may be removed from lower jaw (152) after firing such that the proximal portion of wedge sled (170) may remain disengaged from the input surface of pusher member (166), thereby preventing further closing and/or firing of end effector (410) in the absence of staple cartridge (154).

III. Exemplary Combinations

The following examples relate to various non-exhaustive ways in which the teachings herein may be combined or applied. It should be understood that the following examples are not intended to restrict the coverage of any claims that may be presented at any time in this application or in subsequent filings of this application. No disclaimer is intended. The following examples are being provided for nothing more than merely illustrative purposes. It is contemplated that the various teachings herein may be arranged and applied in numerous other ways. It is also contemplated that some variations may omit certain features referred to in the below examples. Therefore, none of the aspects or features referred to below should be deemed critical unless otherwise explicitly indicated as such at a later date by the inventors or by a successor in interest to the inventors. If any claims are presented in this application or in subsequent filings related to this application that include additional features beyond those referred to below, those additional features shall not be presumed to have been added for any reason relating to patentability.

Example 1

A surgical stapling instrument comprising: (a) a shaft assembly extending along a longitudinal axis to a distal end; (b) an end effector at the distal end of the shaft assembly, wherein the end effector includes: (i) a first jaw having an anvil, (ii) a second jaw configured to removably receive a staple cartridge, and (iii) a driving assembly translatable distally along the longitudinal axis through the second jaw for pivoting the second jaw toward the first jaw to clamp tissue between the first jaw and the second jaw; and (c) a lockout mechanism configured to transition between a first state in which the lockout mechanism prevents distal translation of the driving assembly through the second jaw, and a second state in which the lockout mechanism permits distal translation of the driving assembly through the second jaw, wherein the lockout mechanism is configured to transition from the first state to the second state when the staple cartridge is removably received by the second jaw.

Example 2

The surgical stapling instrument of Example 1, wherein the lockout mechanism comprises: (i) a lever pivotably coupled to the second jaw, and (ii) a protrusion fixedly coupled to the driving assembly, wherein the lever is configured to selectively engage the protrusion.

Example 3

The surgical stapling instrument of Example 2, wherein the lever is configured to engage the protrusion when the lockout mechanism is in the first state for preventing distal translation of the driving assembly through the second jaw, wherein the lever is configured to disengage the protrusion when the lockout mechanism in the second state for permitting distal translation of the driving assembly through the second jaw.

Example 4

The surgical stapling instrument of Example 3, wherein the lever includes a first input surface configured to engage a proximal body portion of the staple cartridge when the staple cartridge is removably received by the second jaw for transitioning the lockout mechanism from the first state toward the second state.

Example 5

The surgical stapling instrument of Example 4, wherein the lever includes a second input surface configured to engage a proximally-positioned wedge sled of the staple cartridge when the staple cartridge is removably received by the second jaw for transitioning the lockout mechanism to the second state.

Example 6

The surgical stapling instrument of any one or more of Examples 3 through 5, wherein the lever is resiliently biased toward engagement with the protrusion.

Example 7

The surgical stapling instrument of Example 2, wherein the lever is configured to engage the protrusion when the lockout mechanism is in the second state for permitting distal translation of the driving assembly through the second jaw, wherein the lever is configured to disengage the protrusion when the lockout mechanism in the first state for preventing distal translation of the driving assembly through the second jaw.

Example 8

The surgical stapling instrument of Example 7, wherein the lever includes an input surface configured to engage a proximally-positioned wedge sled of the staple cartridge when the staple cartridge is removably received by the second jaw for transitioning the lockout mechanism from the first state toward the second state.

Example 9

The surgical stapling instrument of any one or more of Examples 7 through 8, wherein the lever is resiliently biased away from engagement with the protrusion.

Example 10

The surgical stapling instrument of any one or more of Examples 7 through 9, wherein the surgical stapling instrument further comprises a moveable member, wherein the lockout mechanism further comprises a transmission member configured to transmit distal motion from the moveable member to the driving assembly when the lockout mechanism is in the second state, wherein the transmission member is inhibited from transmitting distal motion from the moveable member to the driving assembly when the lockout mechanism is in the first state.

Example 11

The surgical stapling instrument of Example 1, further comprising a moveable member, wherein the lockout mechanism comprises a transmission member coupled to the moveable member, wherein the transmission member is configured to transmit distal motion from the moveable member to the driving assembly when the lockout mechanism is in the second state, wherein the transmission member is inhibited from transmitting distal motion from the moveable member to the driving assembly when the lockout mechanism is in the first state.

Example 12

The surgical stapling instrument of Example 11, wherein the lockout mechanism further comprises a hook coupled to the driving assembly, wherein the hook is configured to selectively engage the transmission member.

Example 13

The surgical stapling instrument of Example 12, wherein the hook is translatable proximally to a predetermined pickup location for engaging the transmission member.

Example 14

The surgical stapling instrument of Example 13, wherein the transmission member is twistable distally to the predetermined pickup location.

Example 15

The surgical stapling instrument of any one or more of Examples 1 through 14, wherein the end effector further includes the staple cartridge, wherein the staple cartridge comprises: (A) a cartridge body, (B) a plurality of staples housed within the cartridge body, and (C) a staple actuator translatable distally through the cartridge body along the longitudinal axis from an initial proximal position, wherein the lockout mechanism is configured to transition from the first state to the second state when the staple cartridge is removably received by the second jaw with the staple actuator at the initial proximal position.

Example 16

A surgical stapling instrument comprising: (a) a shaft assembly extending along a longitudinal axis to a distal end; (b) an end effector at the distal end of the shaft assembly, wherein the end effector includes: (i) a first jaw having an anvil, (ii) a second jaw configured to removably receive a staple cartridge, and (iii) a driving assembly translatable distally along the longitudinal axis through the second jaw for pivoting one of the first jaw or the second jaw toward the other of the first jaw or the second jaw to clamp tissue between the first jaw and the second jaw; (c) an actuation mechanism configured to move distally relative to at least a portion of the shaft assembly, wherein the actuation mechanism is configured to be operatively coupled to the driving assembly for transmitting distal motion to the driving assembly; and (d) a lockout mechanism configured to transition between a first state in which the lockout mechanism prevents distal translation of the driving assembly through the second jaw, and a second state in which the lockout mechanism permits distal translation of the driving assembly through the second jaw, wherein the lockout mechanism is configured to transition from the first state to the second state when the staple cartridge is removably received by the second jaw.

Example 17

A surgical stapling instrument comprising: (a) a shaft assembly extending along a longitudinal axis to a distal end; (b) an end effector at the distal end of the shaft assembly, wherein the end effector includes: (i) a first jaw having an anvil, (ii) a second jaw configured to removably receive a first staple cartridge having a first configuration, and (iii) a driving assembly translatable distally along the longitudinal axis through the second jaw for pivoting the second jaw toward the first jaw to clamp tissue between the first jaw and the second jaw; and (c) at least one lockout mechanism configured to selectively prevent distal translation of the driving assembly through the second jaw when the first staple cartridge is unseated from the second jaw, when a second staple cartridge having a second configuration different from the first configuration is seated within the second jaw, and when the first staple cartridge is seated within the second jaw with a staple actuator of the first staple cartridge located distally relative to an initial proximal position of the staple actuator.

Example 18

The surgical stapling instrument of Example 17, wherein the at least one lockout mechanism includes a first lockout mechanism configured to selectively prevent distal translation of the driving assembly through the second jaw when the first staple cartridge is unseated from the second jaw and when the second staple cartridge is seated within the second jaw, and a second lockout mechanism configured to selectively prevent distal translation of the driving assembly through the second jaw when the first staple cartridge is seated within the second jaw with the staple actuator located distally relative to the initial proximal position.

Example 19

The surgical stapling instrument of Example 17, wherein the at least one lockout mechanism includes a single lockout mechanism having a first lockout feature configured to selectively prevent distal translation of the driving assembly through the second jaw when the first staple cartridge is unseated from the second jaw and when the second staple cartridge is seated within the second jaw, and a second lockout feature configured to selectively prevent distal translation of the driving assembly through the second jaw when the first staple cartridge is seated within the second jaw with the staple actuator located distally relative to the initial proximal position.

Example 20

The surgical stapling instrument of any one or more of Examples 17 through 19, wherein the end effector further includes the first staple cartridge, wherein the first staple cartridge comprises: (A) a cartridge body, (B) a plurality of staples housed within the cartridge body, and (C) the first staple actuator translatable distally through the cartridge body along the longitudinal axis from the initial proximal position.

IV. Miscellaneous

Any one or more of the teachings, expressions, embodiments, examples, etc. described herein may be combined with any one or more of the teachings, expressions, embodiments, examples, etc. described in U.S. patent application Ser. No. 17/402,674, entitled "Methods of Operating a Robotic Surgical Stapler," filed on Aug. 16, 2021, published as U.S. Pub. No. 2023/0051361 on Feb. 16, 2023; U.S. patent application Ser. No. 17/402,675, entitled "Multi-Threshold Motor Control Algorithm for Powered Surgical Stapler," filed on Aug. 16, 2021, published as U.S. Pub. No. 2023/0051271 on Feb. 16, 2023; U.S. patent application Ser. No. 17/402,677, entitled "Variable Response Motor Control Algorithm for Powered Surgical Stapler," filed on Aug. 16, 2021, published as U.S. Pub. No. 2023/0048444 on Feb. 16, 2023; U.S. patent application Ser. No. 17/402,679, entitled "Powered Surgical Stapler Having Independently Operable Closure and Firing Systems," filed on Aug. 16, 2021, issued as U.S. Pat. No. 11,779,332 on Oct. 10, 2023; U.S. patent application Ser. No. 17/402,695, entitled "Firing System Features for Surgical Stapler," filed on Aug. 16, 2021, published as U.S. Pub. No. 2023/0050707 on Feb. 16, 2023; U.S. patent application Ser. No. 17/402,701, entitled "Multiple-Sensor Firing Lockout Mechanism for Powered Surgical Stapler," filed on Aug. 16, 2021, published as U.S. Pub. No. 2023/0050358 on Feb. 16, 2023; U.S. patent application Ser. No. 17/402,703, entitled "Proximally Located Firing Lockout Mechanism for Surgical Stapler," filed on Aug. 16, 2021, published as U.S. Pub. No. 2023/0051105 on Feb. 16, 2023; U.S. patent application Ser. No. 17/402,732, entitled "Sled Restraining Member for Surgical Stapler," filed on Aug. 16, 2021, published as U.S. Pub. No. 2023/00458893 on Feb. 16, 2023; U.S. patent application Ser. No. 17/402,738, entitled "Firing Member Tracking Feature for Surgical Stapler," filed on Aug. 16, 2021, published as U.S. Pub. No. 2023/0049736 on Feb. 16, 2023; U.S. patent application Ser. No. 17/402,744, entitled "Adjustable Power Transmission Mechanism for Powered Surgical Stapler," filed on Aug. 16, 2021, published as U.S. Pub. No. 2023/0051938 on Feb. 16, 2023; U.S. patent application Ser. No. 17/402,749, entitled "Firing Bailout System for Powered Surgical Stapler," filed on Aug. 16, 2021, published as U.S. Pub. No. 2023/0045998 on Feb. 16, 2023; and/or U.S. patent application Ser. No. 17/402,759, entitled "Deflectable Firing Member for Surgical Stapler," filed on Aug. 16, 2021, published as U.S. Pub. No. 2023/0052307 on Feb. 16, 2023. The disclosure of each of these applications is incorporated by reference herein in its entirety.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Versions described above may be designed to be disposed of after a single use, or they can be designed to be used multiple times. Versions may, in either or both cases, be reconditioned for reuse after at least one use. Reconditioning may include any combination of the steps of disassembly of the systems, instruments, and/or portions thereof, followed by cleaning or replacement of particular pieces, and subsequent reassembly. In particular, some versions of the systems, instruments, and/or portions thereof may be disassembled, and any number of the particular pieces or parts of the systems, instruments, and/or portions thereof may be selectively replaced or removed in any combination. Upon cleaning and/or replacement of particular parts, some versions of the systems, instruments, and/or portions thereof may be reassembled for subsequent use either at a reconditioning facility, or by an operator immediately prior to a procedure. Those skilled in the art will appreciate that reconditioning of systems, instruments, and/or portions thereof may utilize a variety of techniques for disassembly, cleaning/replacement, and reassembly. Use of such techniques, and the resulting reconditioned systems, instruments, and/or portions thereof, are all within the scope of the present application.

By way of example only, versions described herein may be sterilized before and/or after a procedure. In one sterilization technique, the systems, instruments, and/or portions thereof is placed in a closed and sealed container, such as a plastic or TYVEK bag. The container and system, instrument, and/or portion thereof may then be placed in a field of radiation that can penetrate the container, such as gamma radiation, x-rays, or high-energy electrons. The radiation may kill bacteria on the system, instrument, and/or portion thereof and in the container. The sterilized systems, instruments, and/or portions thereof may then be stored in the sterile container for later use. Systems, instruments, and/or portions thereof may also be sterilized using any other technique known in the art, including but not limited to beta or gamma radiation, ethylene oxide, or steam.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometries, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:
1. A surgical stapling instrument comprising:
 (a) a shaft assembly extending along a longitudinal axis to a distal end;
 (b) an end effector at the distal end of the shaft assembly, wherein the end effector includes:
  (i) a first jaw having an anvil,
  (ii) a second jaw configured to removably receive a staple cartridge, and
  (iii) a driving assembly translatable distally along the longitudinal axis through the second jaw from a proximal-most position of the driving assembly for pivoting the second jaw toward the first jaw to clamp tissue between the first jaw and the second jaw; and

(c) a lockout mechanism configured to transition between a first state in which the lockout mechanism prevents distal translation of the driving assembly through the second jaw from the proximal-most position of the driving assembly, and a second state in which the lockout mechanism permits distal translation of the driving assembly through the second jaw from the proximal-most position of the driving assembly, wherein the lockout mechanism is configured to transition from the first state to the second state when the staple cartridge is removably received by the second jaw, wherein the lockout mechanism comprises:
(i) a lever pivotably coupled to the second jaw, and
(ii) a protrusion fixedly coupled to the driving assembly, wherein the lever is configured to selectively engage with the protrusion, wherein the lever is configured to engage the protrusion when the lockout mechanism is in the second state for permitting distal translation of the driving assembly through the second jaw, wherein the lever is configured to disengage the protrusion when the lockout mechanism in the first state for preventing distal translation of the driving assembly through the second jaw.

2. The surgical stapling instrument of claim 1, wherein the lever includes an input surface configured to engage a proximally-positioned wedge sled of the staple cartridge when the staple cartridge is removably received by the second jaw for transitioning the lockout mechanism from the first state toward the second state.

3. The surgical stapling instrument of claim 1, wherein the lever is resiliently biased away from engagement with the protrusion.

4. The surgical stapling instrument of claim 1, wherein the surgical stapling instrument further comprises a moveable member, wherein the lockout mechanism further comprises a transmission member configured to transmit distal motion from the moveable member to the driving assembly when the lockout mechanism is in the second state, wherein the transmission member is inhibited from transmitting distal motion from the moveable member to the driving assembly when the lockout mechanism is in the first state.

5. The surgical stapling instrument of claim 1, wherein the end effector further includes the staple cartridge, wherein the staple cartridge comprises:
(A) a cartridge body,
(B) a plurality of staples housed within the cartridge body, and
(C) a staple actuator translatable distally through the cartridge body along the longitudinal axis from an initial proximal position, wherein the lockout mechanism is configured to transition from the first state to the second state when the staple cartridge is removably received by the second jaw with the staple actuator at the initial proximal position.

6. The surgical stapling instrument of claim 1, wherein the lever is rigid.

7. The surgical stapling instrument of claim 1, wherein the lever is directly pivotably coupled to the second jaw.

8. A surgical stapling instrument comprising:
(a) a shaft assembly extending along a longitudinal axis to a distal end;
(b) an end effector at the distal end of the shaft assembly, wherein the end effector includes:
(i) a first jaw having an anvil,
(ii) a second jaw configured to removably receive a staple cartridge, and
(iii) a driving assembly translatable distally along the longitudinal axis through the second jaw from a proximal-most position of the driving assembly for pivoting the second jaw toward the first jaw to clamp tissue between the first jaw and the second jaw;
(c) a lockout mechanism configured to transition between a first state in which the lockout mechanism prevents distal translation of the driving assembly through the second jaw from the proximal-most position of the driving assembly, and a second state in which the lockout mechanism permits distal translation of the driving assembly through the second jaw from the proximal-most position of the driving assembly; and
(d) a movable member;

wherein the lockout mechanism is configured to transition from the first state to the second state when the staple cartridge is removably received by the second jaw, wherein the lockout mechanism comprises a transmission member coupled to the moveable member, wherein the transmission member is configured to transmit distal motion from the moveable member to the driving assembly when the lockout mechanism is in the second state, wherein the transmission member is inhibited from transmitting distal motion from the moveable member to the driving assembly when the lockout mechanism is in the first state.

9. The surgical stapling instrument of claim 8, wherein the lockout mechanism further comprises a hook coupled to the driving assembly, wherein the hook is configured to selectively engage the transmission member.

10. The surgical stapling instrument of claim 9, wherein the hook is translatable proximally to a predetermined pickup location for engaging the transmission member.

11. The surgical stapling instrument of claim 10, wherein the transmission member is twistable distally to the predetermined pickup location.

12. A surgical stapling instrument comprising:
(a) a shaft assembly extending along a longitudinal axis to a distal end;
(b) an end effector at the distal end of the shaft assembly, wherein the end effector includes:
(i) a first jaw having an anvil,
(ii) a second jaw configured to removably receive a first staple cartridge having a first configuration, and
(iii) a driving assembly translatable distally along the longitudinal axis through the second jaw for pivoting the second jaw toward the first jaw to clamp tissue between the first jaw and the second jaw; and
(c) at least one lockout mechanism configured to selectively prevent distal translation of the driving assembly through the second jaw when the first staple cartridge is unseated from the second jaw, when a second staple cartridge having a second configuration different from the first configuration is seated within the second jaw with a staple actuator of the second staple cartridge located at an initial, proximal-most position, and when the first staple cartridge is seated within the second jaw with a staple actuator of the first staple cartridge located distally relative to an initial proximal position of the staple actuator, wherein the at least one lockout mechanism includes a first lockout mechanism configured to selectively prevent distal translation of the driving assembly through the second jaw when the first staple cartridge is unseated from the second jaw and when the second staple cartridge is seated within the second jaw, and a second lockout mechanism configured to selectively prevent distal translation of the driving assembly through the second jaw when the first staple cartridge is seated within the second jaw with the staple actuator located distally relative to the initial proximal position.

13. A surgical stapling instrument comprising:
(a) a shaft assembly extending along a longitudinal axis to a distal end;
(b) an end effector at the distal end of the shaft assembly, wherein the end effector includes:
   (i) a first jaw having an anvil,
   (ii) a second jaw configured to removably receive a first staple cartridge having a first configuration, and
   (iii) a driving assembly translatable distally along the longitudinal axis through the second jaw for pivoting the second jaw toward the first jaw to clamp tissue between the first jaw and the second jaw; and
(c) at least one lockout mechanism configured to selectively prevent distal translation of the driving assembly through the second jaw when the first staple cartridge is unseated from the second jaw, when a second staple cartridge having a second configuration different from the first configuration is seated within the second jaw with a staple actuator of the second staple cartridge located at an initial, proximal-most position, and when the first staple cartridge is seated within the second jaw with a staple actuator of the first staple cartridge located distally relative to an initial proximal position of the staple actuator,
wherein the at least one lockout mechanism includes a single lockout mechanism having a first lockout feature configured to selectively prevent distal translation of the driving assembly through the second jaw when the first staple cartridge is unseated from the second jaw and when the second staple cartridge is seated within the second jaw, and a second lockout feature configured to selectively prevent distal translation of the driving assembly through the second jaw when the first staple cartridge is seated within the second jaw with the staple actuator located distally relative to the initial proximal position.

14. The surgical stapling instrument of claim 12, wherein the end effector further includes the first staple cartridge, wherein the first staple cartridge comprises:
   (A) a cartridge body,
   (B) a plurality of staples housed within the cartridge body, and
   (C) a staple actuator translatable distally through the cartridge body along the longitudinal axis from the initial proximal position.

\* \* \* \* \*